United States Patent
Dolmetsch et al.

(10) Patent No.: US 12,201,612 B2
(45) Date of Patent: Jan. 21, 2025

(54) USE OF MAVOGLURANT IN THE REDUCTION OF ALCOHOL USE OR IN PREVENTING RELAPSE INTO ALCOHOL USE

(71) Applicant: NOVARTIS AG, Basel (CH)

(72) Inventors: Ricardo Carl Elciario Dolmetsch, Concord, MA (US); Fabrizio Gasparini, Weiherhofstrasse (CH); Baltazar Gomez-Mancilla, Basel (CH); Donald Johns, Woburn, MA (US)

(73) Assignee: NOVARTIS AG, Basel (CH)

( * ) Notice: Subject to any disclaimer, the term of this patent is extended or adjusted under 35 U.S.C. 154(b) by 286 days.

(21) Appl. No.: 16/634,986

(22) PCT Filed: Jul. 30, 2018

(86) PCT No.: PCT/IB2018/055665
§ 371 (c)(1),
(2) Date: Jan. 29, 2020

(87) PCT Pub. No.: WO2019/025932
PCT Pub. Date: Feb. 7, 2019

(65) Prior Publication Data
US 2020/0237721 A1 Jul. 30, 2020

Related U.S. Application Data

(60) Provisional application No. 62/539,008, filed on Jul. 31, 2017.

(51) Int. Cl.
*A61K 31/403* (2006.01)
*A61K 45/06* (2006.01)
*A61P 25/32* (2006.01)
(52) U.S. Cl.
CPC ............ *A61K 31/403* (2013.01); *A61K 45/06* (2013.01); *A61P 25/32* (2018.01)
(58) Field of Classification Search
None
See application file for complete search history.

(56) References Cited

U.S. PATENT DOCUMENTS

| | | |
|---|---|---|
| 8,574,626 B2 | 11/2013 | Vergez et al. |
| 8,703,809 B2 | 4/2014 | Gomez-Mancilla et al. |
| 9,770,423 B2 | 9/2017 | Erickson et al. |
| 10,336,687 B2 | 7/2019 | Cacciaglia et al. |
| 2016/0000736 A1 | 1/2016 | Cohen et al. |
| 2016/0128979 A1 | 5/2016 | Thoma et al. |
| 2018/0230086 A1 | 8/2018 | Cacciaglia et al. |
| 2021/0069150 A1 | 3/2021 | Galli et al. |

FOREIGN PATENT DOCUMENTS

| | | |
|---|---|---|
| EP | 1267869 B1 | 5/2004 |
| JP | 2015524805 A | 8/2015 |
| JP | 2016520663 A | 7/2016 |
| WO | 2006/089494 A1 | 8/2006 |
| WO | 2012/117073 A2 | 9/2012 |
| WO | 2015/197079 A1 | 12/2015 |
| WO | 2017021438 A1 | 2/2017 |

OTHER PUBLICATIONS

Bacstrom et al., mGluR5 Antagonist MPEP Reduces Ethanol-Seeking and Relapse Behavior. Neuropsychopharmacology, 2004, 29, 921-928.*
Rehm J. R. The Risks Associated with Alcohol Use and Alcoholism. Alcohol Research & Health, 2011, 34, 135-143.*
McKetin et al., Recreational drug use and binge drinking: Stimulant but not cannabis intoxication is associated with excessive alcohol consumption. Drug and Alcohol Review, 2014, 33, 436-445.*
Haile et al., Genetics of Dopamine and its Contribution to Cocaine Addiction. Behavior Genetics, 2007, 37, 119-145.*
Kiluk et al., Quality versus quantity: acquisition of coping skills following computerized cognitive-behavioral therapy for substance use disorder. Addiction, 2010, 105, 2120-2127.*
Substance Abuse and Mental Health Services Administration and National Institute on Alcohol Abuse and Alcoholism, Medication for the Treatment of Alcohol Use Disorder: A Brief Guide. HHS Publication No. (SMA) 15-4907. Rockville, MD: Substance Abuse and Mental Health Services Administration, 2015.*
Olive et al., "The mGluR5 Antagonist 6-methyl-2-(phenylethynyl)pyridine Decreases Ethanol Consumption via a Protein Kinase C Epsilon-Dependent Mechanism," Mol Pharmacol. 67(2):349-55 (2005).
International Search Report mailed Nov. 6, 2018 for PCT International Application No. PCT/IB2018/055665 (3 pages).
Keck et al., "Fenobam sulfate inhibits cocaine-taking and cocaine-seeking behavior in rats: implications for addiction treatment in humans," Psychopharmacology, Apr. 25, 2013, pp. 253-265, vol. 229, Springer.
Office Action in corresponding JP application 2020-503275 dated Jan. 24, 2023 (pp. 1-3) and English translation thereof.
Parkitna et al.: "Novility Seeking Behaviors and the Escalation of Alcohol Drinking After Abstinence in Mice Are Controlled by Metabolopic Glutamate Receptor 5 on Neurons Expressing Dopamine D1 Receptors", Biol Psychiatry,2013, vol. 73,p. 263-270.
Office Action in corresponding KR application 10-2020-7002167 dated Oct. 10, 2023 (pp. 1-8) and English translation thereof.
Celine Ellen Francois de Esch, "Therapeutic Targets and Translational Endpoints in Fragile X Syndrome" 2014 (pp. 1-142) ISBN: 978-94-6182-448-6.

* cited by examiner

*Primary Examiner* — Po-Chih Chen
(74) *Attorney, Agent, or Firm* — MILLEN, WHITE, ZELANO & BRANIGAN, P.C.; Ryan R. Pool

(57) ABSTRACT

The invention relates to the use of mavoglurant, or a pharmaceutically acceptable salt thereof: in the reduction of alcohol use by an alcohol use disorder patient; in preventing relapse into alcohol use by an alcohol use disorder patient; in the promotion of alcohol abstinence by an alcohol use disorder patient; in the treatment of the symptoms of depression or anxiety associated with alcohol use disorder.

13 Claims, 4 Drawing Sheets

*Figure 1:* Cocaine (0.3 mg/kg/infusion, FR5) self-administration learning curves in Phase I. Rats achieved a stable level of cocaine self-administration during the 15-day acquisition training. Data represent the means + SEM. N=12 per treatment group. 1) Sub-cohort II-a, active lever; 2) Sub-cohort II-b, active lever; 3) Sub-cohort II-a, inactive lever; 4) Sub-cohort II-b, inactive lever.

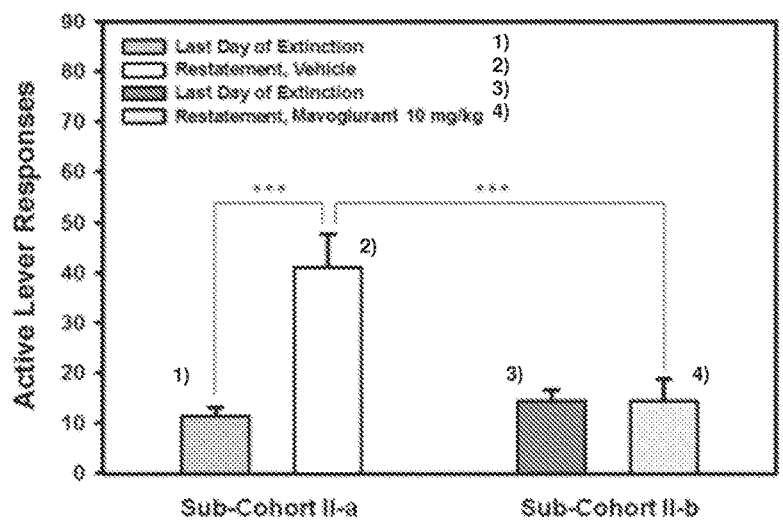
*Figure 4:* Effects of mavoglurant (10 mg/kg, PO, 1 hour pre-treatment) on the reinstatement of a cocaine self-administration response in rats. Data are presented as mean ± SEM. Asterisks (\*\*\*: $P<0.001$) indicate a significant difference. N=14-15 per treatment group. 1) Last day of extinction; 2) Restatement, vehicle; 3) Last day of extinction; 4) Restatement, mavoglurant 10 mg/kg.

USE OF MAVOGLURANT IN THE REDUCTION OF ALCOHOL USE OR IN PREVENTING RELAPSE INTO ALCOHOL USE

The present invention relates to uses of a mGluR5 antagonist.

FIELD OF THE INVENTION

The invention relates to the use of the mGluR5 antagonist named mavoglurant, or a pharmaceutically acceptable salt thereof, in the reduction of alcohol use by an alcohol use disorder patient; in preventing relapse into alcohol use by an alcohol use disorder patient; in the promotion of alcohol abstinence by an alcohol use disorder patient; in the treatment of the symptoms of depression or anxiety associated with alcohol use disorder. In particular, it relates to the use of mavoglurant, or a pharmaceutically acceptable salt thereof, in the reduction of alcohol use/in preventing relapse into alcohol use, by an alcohol use disorder patient.

BACKGROUND OF THE INVENTION

Alcohol use disorder (AUD) is a complex psychiatric disorder, defined with reference to DSM-5 criteria (i.e. according to the Diagnostic and Statistical Manual of Mental Disorders. 5th Edition, Washington, DC: American Psychiatric Association, 2013), which continues to grow into a significant worldwide health problem having adverse medical, social and economic effects. To date, the US Food and Drug Administration (FDA) has approved only three medications for the treatment of AUD, namely disulfiram, naltrexone and acamprosate, and the European Medicines Agency (EMA) has approved, in addition, nalmefene. Due to the heterogeneity of AUD, the efficacy of these medications is only modest, thus there is still a high medical need to find more effective and safe drugs for the treatment of AUD (Alcohol Clin Exp Res, Vol 40, No 7, 2016, 1368-1379). Other pharmacological agents that have been tested include, for example, opioid antagonists (e.g. nalmefene), CB-1 antagonists (e.g. rimonabant), CRH1 receptor antagonists (e.g. verucerfont, pexacerfont), NK1R antagonists (e.g. tradipitant), OTR agonists (e.g. oxytocin), GABA agents (e.g. topiramate, baclofen, benzodiazepines), voltage-gated sodium channel inhibitors (e.g. oxacarbazepine, valproic acid, zonisamide), voltage-dependent calcium channel agonists (e.g. gabapentin, pregabalin), α7 nicotinic acetylcholine receptor agonists (e.g. varenicline), 5-$HT_3$ antagonists (e.g. ondansetron), 5-$HT_{1A}$ receptor partial agonists (e.g. aripiprazole), 5-$HT_{2A}$ receptor antagonists (e.g. quetiapine, olanzapine, mirtazapine), 5-HT reuptake inhibitors (e.g. trazodone), SERT inhibitors (e.g. duloxetine), al adrenoreceptor antagonists (e.g. doxazosin, prazosin), glucocorticoid receptor antagonists (e.g. mifepristone), α1 adrenoreceptor agonists (e.g. guanfacine), AChE inhibitors (e.g. citicoline), a dopamine D2 receptor antagonists (e.g. tiapride) and a α2 adrenoreceptor agonists (e.g. clonidine).

In 1995, English et al published a review (The quantification of drug caused morbidity and mortality in Australia. Commonwealth department of Human Services and Health, Canberra) that discloses health problems shown to be caused by long-term or chronic effects of alcohol consumption. Adverse medical consequences derived from the use of alcohol are, for example, but not limited to, cardiovascular disorders (e.g. hypertension, stroke, cardiac arrhythmias, cardiomyopathy), gastrointestinal disorders (e.g. gastritis, pancreatitis, liver cirrhosis, stomach or duodenal ulcers) and cancer (e.g. oropharyngeal cancer, esophageal cancer, liver cancer, stomach cancer). Further associated health risks include infectious diseases (e.g. hepatitis C or HIV), as well as, serious medical emergencies that can ultimately result in death. In addition, further dangers associated with AUD include risks of accidents, injuries and violence. Moreover, it is common that alcohol use disorder patients present comorbidity with psychiatric disorders, such as depression, anxiety, bipolar disorder and schizophrenia.

The complete biological mechanism of alcohol dependence is not fully understood, yet. Thus, pharmacological treatment of alcohol use disorder has focused on the various stages an alcohol use disorder patient may go through and thus it has aimed to target different aspects, for example: i) attenuate the reinforcing effects of alcohol consumption (e.g. pleasant subjective effects, such as mild euphoria), ii) act as a "substitution treatment" for alcohol, iii) alleviate alcohol withdrawal symptoms (e.g. alcohol craving or anxiety). Pharmacological treatment in AUD can also be divided in three phases: a) from withdrawal to abstinence, whereby the purpose is to lead the patient to quit alcohol consumption (e.g. as provided with benzodiazepines, gabapentin, pregabalin and baclofene treatments), b) abstinence and relapse prevention (e.g. as provided with acamprosate, naltrexone or disulfiram treatments) and c) reduction of alcohol consumption (e.g. as provided with nalmefene treatment).

Finding pharmacotherapies for alcohol use disorder patients are complicated by the high propensity of these patients to relapse (Addiction, 2006, 101, 212-222), thus the rate of early discontinuation from clinical trials is considerably high (Alcohol Clin Exp Res, 1996, 20, 16-20). Therefore, the treatment of alcohol use disorder is a great challenge and a high medical need, in particular, the finding of medications that can help achieve or maintain abstinence from the use of alcohol.

Preclinical models have shown that other mGluR5 antagonists, such as MPEP [i.e. 2-methyl-6-(2-phenylethynyl)pyridine] or such as MTEP [i.e. 3-[2-(2-methylthiazol-4-yl)ethynyl]pyridine] decreased ethanol self-administration in mice (e.g. in Sharko, A. C. et al., Soc. Neurosci. Abstr. 783.781, 2002; in Olive, M. F., et al, Mol. Pharmacol., 2005, 67:349-3550). However, neither MTEP nor MPEP have been further developed due to their shortcomings as therapeutic agents (Keck et al., 2013, Psychopharmacology, 229 (2): 253-65): MTEP shows, for example, potent inhibition of cytochrome P450 1A2 and a rapid metabolism (Smith et al. 2004, Bioorg Med Chem Lett 14:5481-5484) and MPEP shows, for example, off-target effects on NMDA receptors, monoamine oxidase, and the norepinephrine transporter (Cosford et al., J. Med. Chem., 2003, 46 (2), pp 204-206; O'Leary et al., 2000, Br J Pharmacol 131:1429-1437; Heidbreder et al., 2003, Synapse 50:269-276; Lea and Faden, 2006 CNS Drug Rev 12:149-166).

It has been found that mavoglurant may be an ideal candidate for treating patients diagnosed with alcohol use disorder, having therapeutic advantages for said patient population, such as one or more of the following:
  i) it promotes alcohol abstinence, for example, compared to placebo, for example by maintaining abstinence or by reducing the amount or frequency of alcohol use, for example as assessed by urinalysis [e.g. by measuring metabolites of alcohol in urine, such as Ethyl Glucuronide (EtG)] or as assessed by using self-reported alcohol use with standardized tools like the Timeline Follow-Back self-report [Sobell, L. C., Sobell, M. B. (1996) Timeline Followback User's Guide: A Calendar Method for Assessing Alcohol and Drug Use. Addiction Research Foundation, Toronto, Ontario, Canada; *J. Anal. Toxicolo.*, 2002, 26: 393-400];

ii) it decreases relapse into alcohol use, for example, compared to placebo, for example it increases the time to relapse or the rates of patient relapse in a treatment program, such as a clinical trial;

iii) it alleviates (e.g. by eliminating or by reducing intensity, duration or frequency), for example compared to placebo, one or more of symptoms associated with alcohol use disorder selected from:

a. depressive symptoms, for example as assessed from the Beck's Depression Inventory [Beck, A. T. et al., (1961) An inventory for measuring depression. *Archives of General Psychiatry*, 4, 561-571; Beck, A. T. et al., (1988) Psychometric properties of the Beck Depression Inventory: Twenty-five years of evaluation. *Clinical Psychology Review*, 8(1), 77-100]; and b. anxiety symptoms, for example as assessed from the State-Trait Anxiety Inventory [Spielberger, C. D. (1989). *State-Trait Anxiety Inventory: Bibliography* (2$^{nd}$ Ed.). Palo Alto, CA: Consulting Psychologists Press; Spielberger, C. D. et al., (1983). *Manual for the State-Trait Anxiety Inventory*. Palo Alto, CA: Consulting Psychologists Press].

iv) it increases retention of patients in treatment, for example, compared to placebo, for example it increases the rates of patient retention in a treatment program, such as a clinical trial (e.g. as measured by patient attendance at scheduled clinic visits and/or time to dropout from clinical protocol);

v) it improves global functioning, for example as assessed from the Clinical Global Impression Scale-Severity (CGI-S) and Improvement (CGI-I) (Psychiatry, 2007, 4(7): 28-37)

vi) it has a favorable therapeutic profile, such as a favorable safety profile or metabolic profile, for example, a favorable profile in relation to psychiatric adverse events, genotoxicity, or cardiovascular adverse events (e.g. blood pressure, heart rate, electrocardiography parameters); for example, it has better therapeutic profile (e.g. fewer side effects, decreased off-target effects or decreased toxicity, such as decreased genotoxicity) compared to known therapeutic agent/s that have shown efficacy in the treatment of alcohol use disorder; or vii) it has one or more of therapeutic advantages i) to vi), as listed here above, and it also reduces alcohol use, for example, compared to placebo, for example by reducing the amount or frequency of alcohol use, for example as assessed by urinalysis (e.g. measuring metabolites of alcohol, such as ethyl glucuronide) or as assessed by using self-reported alcohol use with standardized tools like the Timeline Follow-Back self-report (*J. Anal. Toxicolo* 2002, 26: 393-400).

SUMMARY OF THE INVENTION

The invention relates to the use of mavoglurant, or a pharmaceutically acceptable salt thereof:
in the reduction of alcohol use by an alcohol use disorder patient;
in preventing relapse into alcohol use by an alcohol use disorder patient;
in the promotion of alcohol abstinence by an alcohol use disorder patient;
in the treatment of the symptoms of depression or anxiety associated with alcohol use disorder.

BRIEF DESCRIPTION OF DRAWINGS

FIG. 4: Effects of mavoglurant (10 mg/kg, PO, 1 hour pre-treatment) on the reinstatement of a cocaine self-administration response in rats. Data are presented as mean+SEM. Asterisks (***: P<0.001) indicate a significant difference. N=14-15 per treatment group.

DETAILED DESCRIPTION OF THE INVENTION

Figure 1:
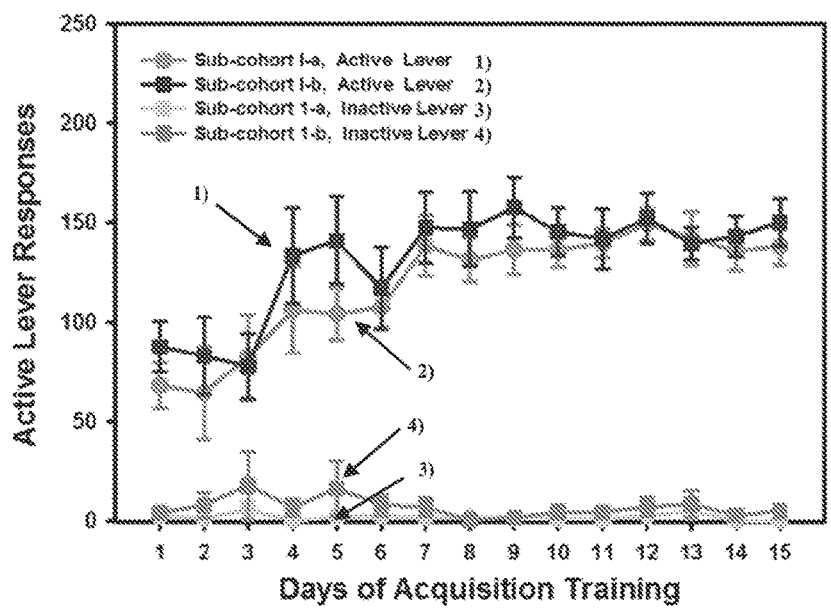
FIG. 1: Cocaine (0.3 mg/kg/infusion, FR5) self-administration learning curves in Phase I. Data represent the means+SEM. N=12 per treatment group.
Figure 2:
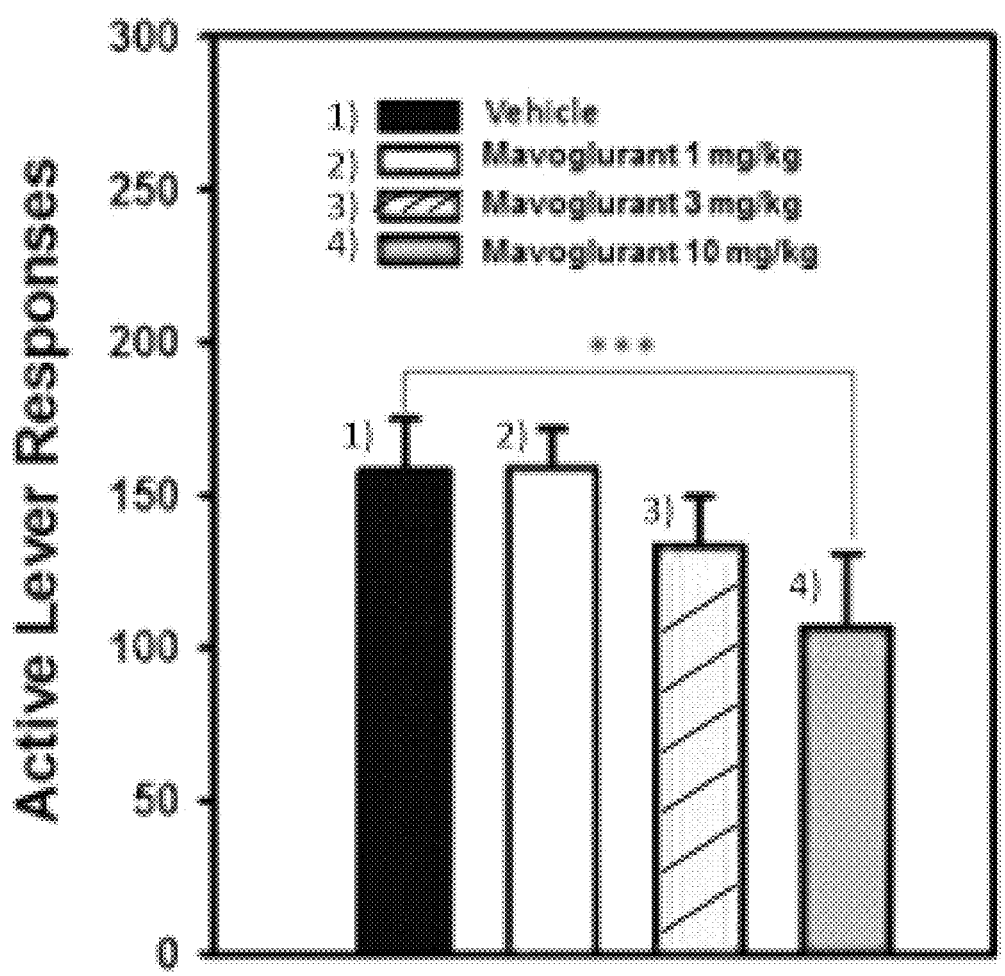
FIG. 2: Acute effects of mavoglurant on cocaine self-administration in two sub-cohorts of rats. Data are presented as mean+SEM. Asterisks (***: P<0.001) indicate significant differences compared to saline or vehicle treatment. N=12 per treatment group.

Embodiments of the present invention are:

Embodiments (a)

1a. Mavoglurant, or a pharmaceutically acceptable salt thereof, for use in the reduction of alcohol use by an alcohol use disorder patient.

2a. Mavoglurant, or a pharmaceutically acceptable salt thereof, for use in preventing relapse into alcohol use by an alcohol use disorder patient.

3a. Mavoglurant, or a pharmaceutically acceptable salt thereof, for use in the promotion of alcohol abstinence by an alcohol use disorder patient.

4a. Mavoglurant, or a pharmaceutically acceptable salt thereof, for use in the treatment of the symptoms of depression or anxiety associated with alcohol use disorder.

5a. Mavoglurant, or a pharmaceutically acceptable salt thereof, for use according to any one of embodiments 1a to 4a, wherein alcohol use disorder is associated with high risk drinking for acute problems (i.e. wherein alcohol use disorder is associated with daily alcohol consumption ≥60 g/day of ethanol for men and ≥40 g/day for women).

6a. Mavoglurant, or a pharmaceutically acceptable salt thereof, for use according to any one of embodiments 1a to 5a, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7a. Mavoglurant, or a pharmaceutically acceptable salt thereof, for use according to any one of embodiments 1a to 6a, wherein the use is combined with standardized psychological treatment, for example, at individual or group level.

8a. Mavoglurant, or a pharmaceutically acceptable salt thereof, for use according to any one of embodiments 1a to 7a, wherein the use is combined with psychosocial or behavioral therapy or combination thereof, in particular contingency management based therapy or 12-step facilitation therapy.

9a. Mavoglurant, or a pharmaceutically acceptable salt thereof, for use according to embodiment 8a, wherein the psychosocial or the behavioral therapy is computer-assisted.

10a. Mavoglurant, or a pharmaceutically acceptable salt thereof, for use according to any one of embodiments 1a to 9a, wherein the use is concomitant with methadone or buprenorphine treatment.

11a. Mavoglurant, or a pharmaceutically acceptable salt thereof, for use according to any one of embodiments 1a to 10a, wherein mavoglurant, or a pharmaceutically acceptable salt thereof, is administered in combination with a further active agent.

12a. Mavoglurant, or a pharmaceutically acceptable salt thereof, for use according to embodiment 11a, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-HT$_3$ antagonist (e.g. ondansetron), a 5-HT$_{1A}$, receptor partial agonist (e.g. aripiprazole), a 5-HT$_{2A}$ receptor antagonist (e.g. quetiapine, olanzapine, mirtazapine), a 5-HT reuptake inhibitor (e.g. trazodone), a SERT inhibitor (e.g. duloxetine), a al adrenoreceptor antagonist (e.g. doxazosin, prazosin), a glucocorticoid receptor antagonist (e.g. mifepristone), a al adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

13a. Mavoglurant, or a pharmaceutically acceptable salt thereof, for use according to any one of embodiments 1a to 12a, wherein the patient has a genetic variation associated with a substance use disorder, such as a genetic variation associated with alcohol use disorder.

14a. Mavoglurant, or a pharmaceutically acceptable salt thereof, for use according to any one of embodiments 1a to 13a, wherein mavoglurant, or a pharmaceutically acceptable salt thereof, is administered in an immediate-release form or a modified-release form.

15a. Mavoglurant, or a pharmaceutically acceptable salt thereof, for use according to any one of embodiments 1a to 14a, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16a. Mavoglurant, or a pharmaceutically acceptable salt thereof, for use according to embodiment 15a, wherein mavoglurant, or a pharmaceutically acceptable salt thereof, is administered with food.

17a. Mavoglurant, or a pharmaceutically acceptable salt thereof, for use according to embodiment 15a or 16a, wherein mavoglurant, or a pharmaceutically acceptable salt thereof, is administered in the morning and in the evening separated by a 12 hour interval.

18a. Mavoglurant, or a pharmaceutically acceptable salt thereof, for use according to any of the preceding embodiments, wherein alcohol use disorder is associated with binge drinking.

Embodiments (b)

1b. A pharmaceutical composition comprising mavoglurant, or a pharmaceutically acceptable salt thereof, and at least one pharmaceutically acceptable excipient, for use in the reduction of alcohol use by an alcohol use disorder patient.

2b. A pharmaceutical composition comprising mavoglurant, or a pharmaceutically acceptable salt thereof, and at least one pharmaceutically acceptable excipient, for use in preventing relapse into alcohol use by an alcohol use disorder patient.

3b. A pharmaceutical composition comprising mavoglurant, or a pharmaceutically acceptable salt thereof, and at least one pharmaceutically acceptable excipient, for use in the promotion of alcohol abstinence by an alcohol use disorder patient.

4b. A pharmaceutical composition comprising mavoglurant, or a pharmaceutically acceptable salt thereof, and at least one pharmaceutically acceptable excipient, for use in the treatment of the symptoms of depression or anxiety associated with alcohol use disorder.

5b. A pharmaceutical composition comprising mavoglurant, or a pharmaceutically acceptable salt thereof, and at least one pharmaceutically acceptable excipient, for use according to any one of embodiments 1 b to 4b, wherein alcohol use disorder is associated with high risk drinking for acute problems (i.e. wherein alcohol use disorder is associated with daily alcohol consumption ≥60 g/day of ethanol for men and ≥40 g/day for women).

6b. A pharmaceutical composition comprising mavoglurant, or a pharmaceutically acceptable salt thereof, and at least one pharmaceutically acceptable excipient, for use according to any one of embodiments 1 b to 5b, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7b. A pharmaceutical composition comprising mavoglurant, or a pharmaceutically acceptable salt thereof, and at least one pharmaceutically acceptable excipient, for use according to any one of embodiments 1 b to 6b, wherein the use is combined with standardized psychological treatment, for example, at individual or group level.

8b. A pharmaceutical composition comprising mavoglurant, or a pharmaceutically acceptable salt thereof, and at least one pharmaceutically acceptable excipient, for use according to any one of embodiments 1 b to 7b, wherein the use is combined with psychosocial or behavioral therapy or combination thereof, in particular contingency management based therapy or 12-step facilitation therapy.

9b. A pharmaceutical composition comprising mavoglurant, or a pharmaceutically acceptable salt thereof, and at least one pharmaceutically acceptable excipient, for use according to embodiment 8b, wherein the psychosocial or the behavioral therapy is computer-assisted.

10b. A pharmaceutical composition comprising mavoglurant, or a pharmaceutically acceptable salt thereof, and at least one pharmaceutically acceptable excipient, for use according to any one of embodiments 1 b to 9b, wherein the use is concomitant with methadone or buprenorphine treatment.

11b. A pharmaceutical composition comprising mavoglurant, or a pharmaceutically acceptable salt thereof, and at least one pharmaceutically acceptable excipient, for use according to any one of embodiments 1 b to 10b, wherein mavoglurant, or a pharmaceutically acceptable salt thereof, is administered in combination with a further active agent.

12b. A pharmaceutical composition comprising mavoglurant, or a pharmaceutically acceptable salt thereof, and at least one pharmaceutically acceptable excipient, for use according to embodiment 11b, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-$HT_3$ antagonist (e.g. ondansetron), a 5-$HT_{1A}$ receptor partial agonist (e.g. aripiprazole), a 5-$HT_{2A}$ receptor antagonist (e.g. quetiapine, olanzapine, mirtazapine), a 5-HT reuptake inhibitor (e.g. trazodone), a SERT inhibitor (e.g. duloxetine), a al adrenoreceptor antagonist (e.g. doxazosin, prazosin), a glucocorticoid receptor antagonist (e.g. mifepristone), a al adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

13b. A pharmaceutical composition comprising mavoglurant, or a pharmaceutically acceptable salt thereof, and at least one pharmaceutically acceptable excipient, for use according to any one of embodiments 1b to 12b, wherein the patient has a genetic variation associated with a substance use disorder, such as a genetic variation associated with alcohol use disorder.

14b. A pharmaceutical composition comprising mavoglurant, or a pharmaceutically acceptable salt thereof, and at least one pharmaceutically acceptable excipient, for use according to any one of embodiments 1b to 13b, which is an immediate-release form or a modified-release form.

15b. A pharmaceutical composition comprising mavoglurant, or a pharmaceutically acceptable salt thereof, and at least one pharmaceutically acceptable excipient, for use according to any one of embodiments 1 b to 14b, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16b. A pharmaceutical composition comprising mavoglurant, or a pharmaceutically acceptable salt thereof, and at least one pharmaceutically acceptable excipient, for use according to embodiment 15b, wherein mavoglurant, or a pharmaceutically acceptable salt thereof, is administered with food.

17b. A pharmaceutical composition comprising mavoglurant, or a pharmaceutically acceptable salt thereof, and at least one pharmaceutically acceptable excipient, for use according to embodiment 15b or 16b, wherein mavoglurant, or a pharmaceutically acceptable salt thereof, is administered in the morning and in the evening separated by a 12 hour interval.

18b. A pharmaceutical composition comprising mavoglurant, or a pharmaceutically acceptable salt thereof, and at least one pharmaceutically acceptable excipient, for use according to any of the preceding embodiments, wherein alcohol use disorder is associated with binge drinking.

Embodiments (c)

1c. A pharmaceutical combination comprising mavoglurant, or a pharmaceutically acceptable salt thereof, and at least one further pharmaceutical active ingredient, for use in the reduction of alcohol use by an alcohol use disorder patient.

2c. A pharmaceutical combination comprising mavoglurant, or a pharmaceutically acceptable salt thereof, and at least one further pharmaceutical active ingredient, for use in preventing relapse into alcohol use by an alcohol use disorder patient.

3c. A pharmaceutical combination comprising mavoglurant, or a pharmaceutically acceptable salt thereof, and at least one further pharmaceutical active ingredient, for use in the promotion of alcohol abstinence by an alcohol use disorder patient.

4c. A pharmaceutical combination comprising mavoglurant, or a pharmaceutically acceptable salt thereof, and at least one further pharmaceutical active ingredient, for use in the treatment of the symptoms of depression or anxiety associated with alcohol use disorder.

5c. A pharmaceutical combination comprising mavoglurant, or a pharmaceutically acceptable salt thereof, and at least one further pharmaceutical active ingredient, for use according to any one of embodiments 1c to 4c, wherein alcohol use disorder is associated with high risk drinking for acute problems (i.e. wherein alcohol use disorder is associated with daily alcohol consumption ≥60 g/day of ethanol for men and ≥40 g/day for women).

6c. A pharmaceutical combination comprising mavoglurant, or a pharmaceutically acceptable salt thereof, and at least one further pharmaceutical active ingredient, for use according to any one of embodiments 1c to 5c, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7c. A pharmaceutical combination comprising mavoglurant, or a pharmaceutically acceptable salt thereof, and at least one further pharmaceutical active ingredient, for use according to any one of embodiments 1c to 6c, wherein the use is combined with standardized psychological treatment, for example, at individual or group level.

8c. A pharmaceutical combination comprising mavoglurant, or a pharmaceutically acceptable salt thereof, and at least one further pharmaceutical active ingredient, for use according to any one of embodiments 1c to 7c, wherein the use is combined with psychosocial or behavioral therapy or combination thereof, in particular contingency management based therapy or 12-step facilitation therapy.

9c. A pharmaceutical combination comprising mavoglurant, or a pharmaceutically acceptable salt thereof, and at least one further pharmaceutical active ingredient, for use according to embodiment 8c, wherein the psychosocial or the behavioral therapy is computer-assisted.

10c. A pharmaceutical combination comprising mavoglurant, or a pharmaceutically acceptable salt thereof, and at least one further pharmaceutical active ingredient, for use according to any one of embodiments 1c to 9c, wherein the use is concomitant with methadone or buprenorphine treatment.

11c. A pharmaceutical combination comprising mavoglurant, or a pharmaceutically acceptable salt thereof, and at least one further pharmaceutical active ingredient, for use according to any one of embodiments 1c to 10c, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-HT$_3$ antagonist (e.g. ondansetron), a 5-HT$_{1A}$, receptor partial agonist (e.g. aripiprazole), a 5-HT$_{2A}$ receptor antagonist (e.g. quetiapine, olanzapine, mirtazapine), a 5-HT reuptake inhibitor (e.g. trazodone), a SERT inhibitor (e.g. duloxetine), a al adrenoreceptor antagonist (e.g. doxazosin, prazosin), a glucocorticoid receptor antagonist (e.g. mifepristone), a al adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

12c. A pharmaceutical combination comprising mavoglurant, or a pharmaceutically acceptable salt thereof, and at least one further pharmaceutical active ingredient, for use according to any one of embodiments 1c to 11c, wherein the patient has a genetic variation associated with a substance use disorder, such as a genetic variation associated with alcohol use disorder.

13c. A pharmaceutical combination comprising mavoglurant, or a pharmaceutically acceptable salt thereof, and at least one further pharmaceutical active ingredient, for use according to any one of embodiments 1c to 12c, wherein mavoglurant, or a pharmaceutically acceptable salt thereof, is administered in an immediate-release form or a modified-release form.

14c. A pharmaceutical combination comprising mavoglurant, or a pharmaceutically acceptable salt thereof, and at least one further pharmaceutical active ingredient, for use according to any one of embodiments 1c to 13c, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

15c. A pharmaceutical combination comprising mavoglurant, or a pharmaceutically acceptable salt thereof, and at least one further pharmaceutical active ingredient, for use according to embodiment 14c, wherein mavoglurant, or a pharmaceutically acceptable salt thereof, is administered with food.

16c. A pharmaceutical combination comprising mavoglurant, or a pharmaceutically acceptable salt thereof, and at least one further pharmaceutical active ingredient, for use according to embodiment 14c or 15c, wherein mavoglurant, or a pharmaceutically acceptable salt thereof, is administered in the morning and in the evening separated by a 12 hour interval.

17c. A pharmaceutical combination comprising mavoglurant, or a pharmaceutically acceptable salt thereof, and at least one further pharmaceutical active ingredient, for use according to any of the preceding embodiments, wherein alcohol use disorder is associated with binge drinking.

Embodiments (d)

1d. Use of mavoglurant, or a pharmaceutically acceptable salt thereof, for the manufacture of a medicament for the reduction of alcohol use by an alcohol use disorder patient.

2d. Use of mavoglurant, or a pharmaceutically acceptable salt thereof, for the manufacture of a medicament for preventing relapse into alcohol use by an alcohol use disorder patient.

3d. Use of mavoglurant, or a pharmaceutically acceptable salt thereof, for the manufacture of a medicament for the promotion of alcohol abstinence by an alcohol use disorder patient.

4d. Use of mavoglurant, or a pharmaceutically acceptable salt thereof, for the manufacture of a medicament for the treatment of the symptoms of depression or anxiety associated with alcohol use disorder.

5d. Use of mavoglurant, or a pharmaceutically acceptable salt thereof, according to any one of embodiments 1d to 4d, wherein alcohol use disorder is associated with high risk drinking for acute problems (i.e. wherein alcohol use disorder is associated with daily alcohol consumption ≥60 g/day of ethanol for men and ≥40 g/day for women).

6d. Use of mavoglurant, or a pharmaceutically acceptable salt thereof, according to any one of embodiments 1d to 5d, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7d. Use of mavoglurant, or a pharmaceutically acceptable salt thereof, according to any one of embodiments 1d to 6d, wherein the use is combined with standardized psychological treatment, for example, at individual or group level.

8d. Use of mavoglurant, or a pharmaceutically acceptable salt thereof, according to any one of embodiments 1d to 7d, wherein the use is combined with psychosocial or behavioral therapy or combination thereof, in particular contingency management based therapy or 12-step facilitation therapy.

9d. Use of mavoglurant, or a pharmaceutically acceptable salt thereof, according to embodiment 8d, wherein the psychosocial or the behavioral therapy is computer-assisted.

10d. Use of mavoglurant, or a pharmaceutically acceptable salt thereof, according to any one of embodiments 1d to 9d, wherein the use is concomitant with methadone or buprenorphine treatment.

11d. Use of mavoglurant, or a pharmaceutically acceptable salt thereof, according to any one of embodiments 1d to 10d, wherein mavoglurant, or a pharmaceutically acceptable salt thereof, is administered in combination with a further active agent.

12d. Use of mavoglurant, or a pharmaceutically acceptable salt thereof, according to embodiment 11d, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-HT$_3$ antagonist (e.g. ondansetron), a 5-HT$_{1A}$, receptor partial agonist (e.g. aripiprazole), a 5-HT$_{2A}$ receptor antagonist (e.g. quetiapine, olanzapine, mirtazapine), a 5-HT reuptake inhibitor (e.g.

trazodone), a SERT inhibitor (e.g. duloxetine), a α1 adrenoreceptor antagonist (e.g. doxazosin, prazosin), a glucocorticoid receptor antagonist (e.g. mifepristone), a α1 adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

13d. Use of mavoglurant, or a pharmaceutically acceptable salt thereof, according to any one of embodiments 1d to 12d, wherein the patient has a genetic variation associated with a substance use disorder, such as a genetic variation associated with alcohol use disorder.

14d. Use of mavoglurant, or a pharmaceutically acceptable salt thereof, according to any one of embodiments 1d to 13d, wherein mavoglurant, or a pharmaceutically acceptable salt thereof, is administered in an immediate-release form or a modified-release form.

15d. Use of mavoglurant, or a pharmaceutically acceptable salt thereof, according to any one of embodiments 1d to 14d, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16d. Use of mavoglurant, or a pharmaceutically acceptable salt thereof, according to embodiment 15d, wherein mavoglurant, or a pharmaceutically acceptable salt thereof, is administered with food.

17d. Use of mavoglurant, or a pharmaceutically acceptable salt thereof, according to embodiment 15d or 16d, wherein mavoglurant, or a pharmaceutically acceptable salt thereof, is administered in the morning and in the evening separated by a 12 hour interval.

18d. Use of mavoglurant, or a pharmaceutically acceptable salt thereof, according to any of the preceding embodiments, wherein alcohol use disorder is associated with binge drinking.

Embodiments (e)

1e. Use of a pharmaceutical composition comprising mavoglurant, or a pharmaceutically acceptable salt thereof, and at least one pharmaceutically acceptable excipient, for the manufacture of a medicament for the reduction of alcohol use by an alcohol use disorder patient.

2e. Use of a pharmaceutical composition comprising mavoglurant, or a pharmaceutically acceptable salt thereof, and at least one pharmaceutically acceptable excipient, for the manufacture of a medicament for preventing relapse into alcohol use by an alcohol use disorder patient.

3e. Use of a pharmaceutical composition comprising mavoglurant, or a pharmaceutically acceptable salt thereof, and at least one pharmaceutically acceptable excipient, for the manufacture of a medicament for the promotion of alcohol abstinence by an alcohol use disorder patient.

4e. Use of a pharmaceutical composition comprising mavoglurant, or a pharmaceutically acceptable salt thereof, and at least one pharmaceutically acceptable excipient, for the manufacture of a medicament for the treatment of the symptoms of depression or anxiety associated with alcohol use disorder.

5e. Use of a pharmaceutical composition comprising mavoglurant, or a pharmaceutically acceptable salt thereof, and at least one pharmaceutically acceptable excipient, according to any one of embodiments 1e to 4e, wherein alcohol use disorder is associated with high risk drinking for acute problems (i.e. wherein alcohol use disorder is associated with daily alcohol consumption ≥60 g/day of ethanol for men and ≥40 g/day for women).

6e. Use of a pharmaceutical composition comprising mavoglurant, or a pharmaceutically acceptable salt thereof, and at least one pharmaceutically acceptable excipient, according to any one of embodiments 1e to 5e, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7e. Use of a pharmaceutical composition comprising mavoglurant, or a pharmaceutically acceptable salt thereof, and at least one pharmaceutically acceptable excipient, according to any one of embodiments 1e to 6e, wherein the use is combined with standardized psychological treatment, for example, at individual or group level.

8e. Use of a pharmaceutical composition comprising mavoglurant, or a pharmaceutically acceptable salt thereof, and at least one pharmaceutically acceptable excipient, according to any one of embodiments 1e to 7e, wherein the use is combined with psychosocial or behavioral therapy or combination thereof, in particular contingency management based therapy or 12-step facilitation therapy.

9e. Use of a pharmaceutical composition comprising mavoglurant, or a pharmaceutically acceptable salt thereof, and at least one pharmaceutically acceptable excipient, according to embodiment 8e, wherein the psychosocial or the behavioral therapy is computer-assisted.

10e. Use of a pharmaceutical composition comprising mavoglurant, or a pharmaceutically acceptable salt thereof, and at least one pharmaceutically acceptable excipient, according to any one of embodiments 1e to 9e, wherein the use is concomitant with methadone or buprenorphine treatment.

11e. Use of a pharmaceutical composition comprising mavoglurant, or a pharmaceutically acceptable salt thereof, and at least one pharmaceutically acceptable excipient, according to any one of embodiments 1e to 10e, wherein mavoglurant, or a pharmaceutically acceptable salt thereof, is administered in combination with a further active agent.

12e. Use of a pharmaceutical composition comprising mavoglurant, or a pharmaceutically acceptable salt thereof, and at least one pharmaceutically acceptable excipient, according to embodiment 11e, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-HT$_3$ antagonist (e.g. ondansetron), a 5-HT$_{1A}$ receptor partial agonist (e.g. aripiprazole), a 5-HT$_{2A}$ receptor antagonist (e.g. quetiapine, olanzapine, mirtazapine), a 5-HT reuptake inhibitor (e.g. trazodone), a SERT inhibitor (e.g. duloxetine), a α1 adrenoreceptor antagonist (e.g. doxazosin, prazosin), a glucocorticoid receptor antagonist (e.g. mifepristone), a α1 adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g.

acamprosate) and an aldehyde dehydrogenase inhibitor (e.g. disulfiram); or pharmaceutically acceptable salts thereof.

13e. Use of a pharmaceutical composition comprising mavoglurant, or a pharmaceutically acceptable salt thereof, and at least one pharmaceutically acceptable excipient, according to any one of embodiments 1e to 12e, wherein the patient has a genetic variation associated with a substance use disorder, such as a genetic variation associated with alcohol use disorder.

14e. Use of a pharmaceutical composition comprising mavoglurant, or a pharmaceutically acceptable salt thereof, and at least one pharmaceutically acceptable excipient, according to any one of embodiments 1e to 13e, which is an immediate-release form or a modified-release form.

15e. Use of a pharmaceutical composition comprising mavoglurant, or a pharmaceutically acceptable salt thereof, and at least one pharmaceutically acceptable excipient, according to any one of embodiments 1e to 14e, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16e. Use of a pharmaceutical composition comprising mavoglurant, or a pharmaceutically acceptable salt thereof, and at least one pharmaceutically acceptable excipient, according to embodiment 15e, wherein mavoglurant, or a pharmaceutically acceptable salt thereof, is administered with food.

17e. Use of a pharmaceutical composition comprising mavoglurant, or a pharmaceutically acceptable salt thereof, and at least one pharmaceutically acceptable excipient, according to embodiment 15e or 16e, wherein mavoglurant, or a pharmaceutically acceptable salt thereof, is administered in the morning and in the evening separated by a 12 hour interval.

18e. Use of a pharmaceutical composition comprising mavoglurant, or a pharmaceutically acceptable salt thereof, and at least one pharmaceutically acceptable excipient, according to any of the preceding embodiments, wherein alcohol use disorder is associated with binge drinking.

Embodiments (f)

1f. Use of a pharmaceutical combination comprising mavoglurant, or a pharmaceutically acceptable salt thereof, and at least one further pharmaceutical active ingredient, for the manufacture of a medicament for the reduction of alcohol use by an alcohol use disorder patient.

2f. Use of a pharmaceutical combination comprising mavoglurant, or a pharmaceutically acceptable salt thereof, and at least one further pharmaceutical active ingredient, for the manufacture of a medicament for preventing relapse into alcohol use by an alcohol use disorder patient.

3f. Use of a pharmaceutical combination comprising mavoglurant, or a pharmaceutically acceptable salt thereof, and at least one further pharmaceutical active ingredient, for the manufacture of a medicament for the promotion of alcohol abstinence by an alcohol use disorder patient.

4f. Use of a pharmaceutical combination comprising mavoglurant, or a pharmaceutically acceptable salt thereof, and at least one further pharmaceutical active ingredient, for the manufacture of a medicament for the treatment of the symptoms of depression or anxiety associated with alcohol use disorder.

5f. Use of a pharmaceutical combination comprising mavoglurant, or a pharmaceutically acceptable salt thereof, and at least one further pharmaceutical active ingredient, according to any one of embodiments 1f to 4f, wherein alcohol use disorder is associated with high risk drinking for acute problems (i.e. wherein alcohol use disorder is associated with daily alcohol consumption ≥60 g/day of ethanol for men and ≥40 g/day for women).

6f. Use of a pharmaceutical combination comprising mavoglurant, or a pharmaceutically acceptable salt thereof, and at least one further pharmaceutical active ingredient, according to any one of embodiments 1f to 5f, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7f. Use of a pharmaceutical combination comprising mavoglurant, or a pharmaceutically acceptable salt thereof, and at least one further pharmaceutical active ingredient, according to any one of embodiments 1f to 6f, wherein the use is combined with standardized psychological treatment, for example, at individual or group level.

8f. Use of a pharmaceutical combination comprising mavoglurant, or a pharmaceutically acceptable salt thereof, and at least one further pharmaceutical active ingredient, according to any one of embodiments 1f to 7f, wherein the use is combined with psychosocial or behavioral therapy or combination thereof, in particular contingency management based therapy or 12-step facilitation therapy.

9f. Use of a pharmaceutical combination comprising mavoglurant, or a pharmaceutically acceptable salt thereof, and at least one further pharmaceutical active ingredient, according embodiment 8f, wherein the psychosocial or the behavioral therapy is computer-assisted.

10f. Use of a pharmaceutical combination comprising mavoglurant, or a pharmaceutically acceptable salt thereof, and at least one further pharmaceutical active ingredient, according to any one of embodiments 1f to 9f, wherein the use is concomitant with methadone or buprenorphine treatment.

11f. Use of a pharmaceutical combination comprising mavoglurant, or a pharmaceutically acceptable salt thereof, and at least one further pharmaceutical active ingredient, according to any one of embodiments 1f to 10f, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a $5\text{-}HT_3$ antagonist (e.g. ondansetron), a $5\text{-}HT_{1A}$ receptor partial agonist (e.g. aripiprazole), a $5\text{-}HT_{2A}$ receptor antagonist (e.g. quetiapine, olanzapine, mirtazapine), a 5-HT reuptake inhibitor (e.g. trazodone), a SERT inhibitor (e.g. duloxetine), a a1 adrenoreceptor antagonist (e.g. doxazosin, prazosin), a glucocorticoid receptor antagonist (e.g. mifepristone), a a1 adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

12f. Use of a pharmaceutical combination comprising mavoglurant, or a pharmaceutically acceptable salt thereof, and at least one further pharmaceutical active ingredient, according to any one of embodiments 1f to 11f, wherein the patient has a genetic variation associated with a substance use disorder, such as a genetic variation associated with alcohol use disorder.

13f. Use of a pharmaceutical combination comprising mavoglurant, or a pharmaceutically acceptable salt thereof, and at least one further pharmaceutical active ingredient, according to any one of embodiments 1f to 12f, wherein mavoglurant, or a pharmaceutically acceptable salt thereof, is administered in an immediate-release form or a modified-release form.

14f. Use of a pharmaceutical combination comprising mavoglurant, or a pharmaceutically acceptable salt thereof, and at least one further pharmaceutical active ingredient, according to any one of embodiments 1c to 13c, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

15f. Use of a pharmaceutical combination comprising mavoglurant, or a pharmaceutically acceptable salt thereof, and at least one further pharmaceutical active ingredient, according to embodiment 14f, wherein mavoglurant, or a pharmaceutically acceptable salt thereof, is administered with food.

16f. Use of a pharmaceutical combination comprising mavoglurant, or a pharmaceutically acceptable salt thereof, and at least one further pharmaceutical active ingredient, according to embodiment 14f or 15f, wherein mavoglurant, or a pharmaceutically acceptable salt thereof, is administered in the morning and in the evening separated by a 12 hour interval.

17f. Use of a pharmaceutical combination comprising mavoglurant, or a pharmaceutically acceptable salt thereof, and at least one further pharmaceutical active ingredient, according to any of the preceding embodiments, wherein alcohol use disorder is associated with binge drinking.

Embodiments (o)

1g. A method for the reduction of alcohol use by an alcohol use disorder patient, in need thereof, comprising administering to said alcohol use disorder patient an effective amount of mavoglurant, or a pharmaceutically acceptable salt thereof.

2g. A method for preventing relapse into alcohol use by an alcohol use disorder patient, in need thereof, comprising administering to said alcohol use disorder patient an effective amount of mavoglurant, or a pharmaceutically acceptable salt thereof.

3g. A method for the promotion of alcohol abstinence by an alcohol use disorder patient, in need thereof, comprising administering to said alcohol use disorder patient an effective amount of mavoglurant, or a pharmaceutically acceptable salt thereof.

4g. A method for treating the symptoms of depression or anxiety associated with alcohol use disorder by an alcohol use disorder patient, in need thereof, comprising administering to said alcohol use disorder patient an effective amount of mavoglurant, or a pharmaceutically acceptable salt thereof.

5g. A method according to any one of embodiments 1g to 4g, wherein alcohol use disorder is associated with high risk drinking for acute problems (i.e. wherein alcohol use disorder is associated with daily alcohol consumption ≥60 g/day of ethanol for men and ≥40 g/day for women).

6g. A method according to any one of embodiments 1g to 5g, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7g. A method according to any one of embodiments 1g to 6g, wherein administration of mavoglurant, or a pharmaceutically acceptable salt thereof is combined with standardized psychological treatment, for example, at individual or group level.

8g. A method according to any one of embodiments 1g to 7g, wherein administration of mavoglurant, or a pharmaceutically acceptable salt thereof is combined is combined with psychosocial or behavioral therapy or combination thereof, in particular contingency management based therapy or 12-step facilitation therapy.

9g. A method according to embodiment 8g, wherein the psychosocial or the behavioral therapy is computer-assisted.

10g. A method according to any one of embodiments 1g to 9g, wherein administration of mavoglurant, or a pharmaceutically acceptable salt thereof, is concomitant with methadone or buprenorphine treatment.

11g. A method according to any one of embodiments 1g to 10g, wherein mavoglurant, or a pharmaceutically acceptable salt thereof, is administered in combination with a further active agent.

12g. A method according to embodiment 11g, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-$HT_3$ antagonist (e.g. ondansetron), a 5-$HT_{1A}$ receptor partial agonist (e.g. aripiprazole), a 5-$HT_{2A}$ receptor antagonist (e.g. quetiapine, olanzapine, mirtazapine), a 5-HT reuptake inhibitor (e.g. trazodone), a SERT inhibitor (e.g. duloxetine), a al adrenoreceptor antagonist (e.g. doxazosin, prazosin), a glucocorticoid receptor antagonist (e.g. mifepristone), a al adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

13g. A method according to any one of embodiments 1g to 12g, wherein the patient has a genetic variation associated with a substance use disorder, such as a genetic variation associated with alcohol use disorder.

14g. A method according to any one of embodiments 1g to 13g, wherein mavoglurant, or a pharmaceutically acceptable salt thereof, is administered in an immediate-release form or a modified-release form.

15g. A method according to any one of embodiments 1g to 14g, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16g. A method according to embodiment 15g, wherein mavoglurant, or a pharmaceutically acceptable salt thereof, is administered with food.

17g. A method according to embodiment 15g or 16g, wherein mavoglurant, or a pharmaceutically acceptable salt thereof, is administered in the morning and in the evening separated by a 12 hour interval.

18g. A method according to any of the preceding embodiments, wherein alcohol use disorder is associated with binge drinking.

Embodiments (h)

1h. A method for the reduction of alcohol use by an alcohol use disorder patient, in need thereof, comprising administering to said alcohol use disorder patient a pharmaceutical composition comprising an effective amount of mavoglurant, or a pharmaceutically acceptable salt thereof, and at least one pharmaceutically acceptable excipient.

2h. A method for preventing relapse into alcohol use by an alcohol use disorder patient, in need thereof, comprising administering to said alcohol use disorder patient a pharmaceutical composition comprising an effective amount of mavoglurant, or a pharmaceutically acceptable salt thereof, and at least one pharmaceutically acceptable excipient.

3h. A method for the promotion of alcohol abstinence by an alcohol use disorder patient, in need thereof, comprising administering to said alcohol use disorder patient a pharmaceutical composition comprising an effective amount of mavoglurant, or a pharmaceutically acceptable salt thereof, and at least one pharmaceutically acceptable excipient.

4h. A method for treating the symptoms of depression or anxiety associated with alcohol use disorder by an alcohol use disorder patient, in need thereof, comprising administering to said alcohol use disorder patient a pharmaceutical composition comprising an effective amount of mavoglurant, or a pharmaceutically acceptable salt thereof, and at least one pharmaceutically acceptable excipient.

5h. A method according to any one of embodiments 1h to 4h, wherein alcohol use disorder is associated with high risk drinking for acute problems (i.e. wherein alcohol use disorder is associated with daily alcohol consumption ≥60 g/day of ethanol for men and ≥40 g/day for women).

6h. A method according to any one of embodiments 1h to 5h, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7h. A method according to any one of embodiments 1h to 6h, wherein administration of the pharmaceutical composition comprising an effective amount of mavoglurant, or a pharmaceutically acceptable salt thereof, and at least one pharmaceutically acceptable excipient, is combined with standardized psychological treatment, for example, at individual or group level.

8h. A method according to any one of embodiments 1h to 7h, wherein administration of the pharmaceutical composition comprising an effective amount of mavoglurant, or a pharmaceutically acceptable salt thereof, and at least one pharmaceutically acceptable excipient, is combined with psychosocial or behavioral therapy or combination thereof, in particular contingency management based therapy or 12-step facilitation therapy.

9h. A method according to embodiment 8h, wherein the psychosocial or behavioral therapy is computer-assisted.

10h. A method according to any one of embodiments 1h to 9h, wherein administration of the pharmaceutical composition comprising an effective amount of mavoglurant, or a pharmaceutically acceptable salt thereof, and at least one pharmaceutically acceptable excipient, is concomitant with methadone or buprenorphine treatment.

11h. A method according to any one of embodiments 1h to 10h, wherein mavoglurant, or a pharmaceutically acceptable salt thereof, is administered in combination with a further active agent.

12h. A method according to embodiment 11h, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-$HT_3$ antagonist (e.g. ondansetron), a 5-$HT_{1A}$ receptor partial agonist (e.g. aripiprazole), a 5-$HT_{2A}$ receptor antagonist (e.g. quetiapine, olanzapine, mirtazapine), a 5-HT reuptake inhibitor (e.g. trazodone), a SERT inhibitor (e.g. duloxetine), a α1 adrenoreceptor antagonist (e.g. doxazosin, prazosin), a glucocorticoid receptor antagonist (e.g. mifepristone), a α1 adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

13h. A method according to any one of embodiments 1h to 12h, wherein the patient has a genetic variation associated with a substance use disorder, such as a genetic variation associated with alcohol use disorder.

14h. A method according to any one of embodiments 1h to 13h, wherein the pharmaceutical composition comprising mavoglurant, or a pharmaceutically acceptable salt thereof, and at least one pharmaceutically acceptable excipient, is an immediate-release form or a modified-release form.

15h. A method according to any one of embodiments 1h to 14h, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16h. A method according to embodiment 15h, wherein the pharmaceutical composition comprising an effective amount of mavoglurant, or a pharmaceutically acceptable salt thereof, and at least one pharmaceutically acceptable excipient, is administered with food.

17h. A method according to embodiment 15h or 16h, wherein the pharmaceutical composition comprising an effective amount of mavoglurant, or a pharmaceutically acceptable salt thereof, and at least one pharmaceutically acceptable excipient, is administered in the morning and in the evening separated by a 12 hour interval.

18h. A method according to any of the preceding embodiments, wherein alcohol use disorder is associated with binge drinking.

Embodiments (j)

1j. A method for the reduction of alcohol use by an alcohol use disorder patient, in need thereof, comprising administering to said alcohol use disorder patient a pharmaceutical combination comprising an effective amount of mavoglurant, or a pharmaceutically acceptable salt thereof, and at least one further pharmaceutical active ingredient.

2j. A method for preventing relapse into alcohol use by an alcohol use disorder patient, in need thereof, comprising administering to said alcohol use disorder patient a pharmaceutical combination comprising an effective amount of mavoglurant, or a pharmaceutically acceptable salt thereof, and at least one at least one further pharmaceutical active ingredient.

3j. A method for the promotion of alcohol abstinence by an alcohol use disorder patient, in need thereof, comprising administering to said alcohol use disorder patient a pharmaceutical combination comprising an effective amount of mavoglurant, or a pharmaceutically acceptable salt thereof, and at least one at least one further pharmaceutical active ingredient.

4j. A method for treating the symptoms of depression or anxiety associated with alcohol use disorder by an alcohol use disorder patient, in need thereof, comprising administering to said alcohol use disorder patient a pharmaceutical combination comprising an effective amount of mavoglurant, or a pharmaceutically acceptable salt thereof, and at least one at least one further pharmaceutical active ingredient.

5j. A method according to any one of embodiments 1j to 4j, wherein alcohol use disorder is associated with high risk drinking for acute problems (i.e. wherein alcohol use disorder is associated with daily alcohol consumption ≥60 g/day of ethanol for men and ≥40 g/day for women).

6j. A method according to any one of embodiments 1j to 5j, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7j. A method according to any one of embodiments 1j to 6j, wherein administration of the pharmaceutical combination comprising an effective amount of mavoglurant, or a pharmaceutically acceptable salt thereof, and at least one further pharmaceutical active ingredient, is combined with standardized psychological treatment, for example, at individual or group level.

8j. A method according to any one of embodiments 1j to 7j, wherein administration of the pharmaceutical combination comprising an effective amount of mavoglurant, or a pharmaceutically acceptable salt thereof, and at least one further pharmaceutical active ingredient, is combined with psychosocial or behavioral therapy or combination thereof, in particular contingency management based therapy or 12-step facilitation therapy.

9j. A method according to embodiment 8j, wherein the psychosocial or the behavioral therapy is computer-assisted.

10j. A method according to any one of embodiments 1j to 9j, wherein administration of the pharmaceutical combination comprising an effective amount of mavoglurant, or a pharmaceutically acceptable salt thereof, and at least one further pharmaceutical active ingredient, is concomitant with methadone or buprenorphine treatment.

11j. A method according to embodiment 10j, wherein the further active agent is selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-HT$_3$ antagonist (e.g. ondansetron), a 5-HT$_{1A}$ receptor partial agonist (e.g. aripiprazole), a 5-HT$_{2A}$ receptor antagonist (e.g. quetiapine, olanzapine, mirtazapine), a 5-HT reuptake inhibitor (e.g. trazodone), a SERT inhibitor (e.g. duloxetine), a α1 adrenoreceptor antagonist (e.g. doxazosin, prazosin), a glucocorticoid receptor antagonist (e.g. mifepristone), a α1 adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

12j. A method according to any one of embodiments 1j to 11j, wherein the patient has a genetic variation associated with a substance use disorder, such as a genetic variation associated with alcohol use disorder.

13j. A method according to any one of embodiments 1j to 12j, wherein the pharmaceutical combination comprising mavoglurant, or a pharmaceutically acceptable salt thereof, and at least one further pharmaceutical active ingredient, is an immediate-release form or a modified-release form.

14j. A method according to any one of embodiments 1j to 13j, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

15j. A method according to embodiment 14j, wherein the pharmaceutical combination comprising an effective amount of mavoglurant, or a pharmaceutically acceptable salt thereof, and at least one further pharmaceutical active ingredient, is administered with food.

16j. A method according to embodiment 14j or 15j, wherein the pharmaceutical combination comprising an effective amount of mavoglurant, or a pharmaceutically acceptable salt thereof, and at least one further pharmaceutical active ingredient, is administered in the morning and in the evening separated by a 12 hour interval.

17j. A method according to any of the preceding embodiments, wherein alcohol use disorder is associated with binge drinking.

FURTHER EMBODIMENTS

Embodiment 1: Mavoglurant, or a pharmaceutically acceptable salt thereof, for use in the reduction of alcohol use by an alcohol use disorder patient.

Embodiment 2: Mavoglurant, or a pharmaceutically acceptable salt thereof, for use in preventing relapse into alcohol use by an alcohol use disorder patient.

Embodiment 3: Mavoglurant, or a pharmaceutically acceptable salt thereof, for use in the promotion of alcohol abstinence by an alcohol use disorder patient.

Embodiment 4: Mavoglurant, or a pharmaceutically acceptable salt thereof, for use in the treatment of the symptoms of depression or anxiety associated with alcohol use disorder.

Embodiment 5: Mavoglurant, or a pharmaceutically acceptable salt thereof, for use according to any one of embodiments 1 to 4, wherein alcohol use disorder is associated with high risk drinking for acute problems (i.e.

wherein alcohol use disorder is associated with daily alcohol consumption ≥60 g/day of ethanol for men and ≥40 g/day for women).

Embodiment 6: Mavoglurant, or a pharmaceutically acceptable salt thereof, for use according to any one of embodiments 1 to 5, wherein alcohol use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

Embodiment 7: Mavoglurant, or a pharmaceutically acceptable salt thereof, for use according to any one of embodiments 1 to 6, wherein the use is combined with standardized psychological treatment, for example, at individual or group level.

Embodiment 8: Mavoglurant, or a pharmaceutically acceptable salt thereof, for use according to any one of embodiments 1 to 7, wherein the use is combined with psychosocial or behavioral therapy or combination thereof, in particular contingency management based therapy or 12-step facilitation therapy.

Embodiment 9: Mavoglurant, or a pharmaceutically acceptable salt thereof, for use according to embodiment 8, wherein the psychosocial or the behavioral therapy is computer-assisted.

Embodiment 10: Mavoglurant, or a pharmaceutically acceptable salt thereof, for use according to any one of embodiments 1 to 9, wherein the use is concomitant with methadone or buprenorphine treatment.

Embodiment 11: Mavoglurant, or a pharmaceutically acceptable salt thereof, for use according to any one of embodiments 1 to 10, wherein mavoglurant, or a pharmaceutically acceptable salt thereof, is administered in combination with a further active agent.

Embodiment 12: Mavoglurant, or a pharmaceutically acceptable salt thereof, for use according to any one of embodiments 1 to 11, wherein the patient has a genetic variation associated with a substance use disorder, such as a genetic variation associated with alcohol use disorder.

Embodiment 13: Mavoglurant, or a pharmaceutically acceptable salt thereof, for use according to any one of embodiments 1 to 12, wherein mavoglurant, or a pharmaceutically acceptable salt thereof, is administered in an immediate-release form or a modified-release form.

Embodiment 14: Mavoglurant, or a pharmaceutically acceptable salt thereof, for use according to any one of embodiments 1 to 13, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

Embodiment 15: Mavoglurant, or a pharmaceutically acceptable salt thereof, for use according to any of the preceding embodiments, wherein alcohol use disorder is associated with binge drinking.

Embodiment 16: A combination comprising mavoglurant, or a pharmaceutically acceptable salt thereof, and at least one further active agent selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-$HT_3$ antagonist (e.g. ondansetron), a 5-$HT_{1A}$ receptor partial agonist (e.g. aripiprazole), a 5-$HT_{2A}$ receptor antagonist (e.g. quetiapine, olanzapine, mirtazapine), a 5-HT reuptake inhibitor (e.g. trazodone), a SERT inhibitor (e.g. duloxetine), a α1 adrenoreceptor antagonist (e.g. doxazosin, prazosin), a glucocorticoid receptor antagonist (e.g. mifepristone), a α1 adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof General Terms The term "alcohol use disorder" or "AUD", as used herein, is defined with reference to DSM-5 criteria (i.e. according to the Diagnostic and Statistical Manual of Mental Disorders. 5th Edition, Washington, DC: American Psychiatric Association, 2013), the entire contents of which are incorporated herein by reference. As used herein, the term "alcohol use disorder" is defined as a problematic pattern of alcohol use leading to clinically significant impairment or distress, as manifested by at least two of the following, occurring within a 12-month period:

1) Alcohol is often taken in larger amounts or over a longer period than was intended.

2) There is a persistent desire or unsuccessful efforts to cut down or control alcohol use.

3) A great deal of time is spent in activities necessary to obtain alcohol, use alcohol, or recover from its effects.

4) Craving, or a strong desire or urge to use alcohol.

5) Recurrent alcohol use resulting in a failure to fulfill major role obligations at work, school, or home.

6) Continued alcohol use despite having persistent or recurrent social or interpersonal problems caused or exacerbated by the effects of alcohol.

7) Important social, occupational, or recreational activities are given up or reduced because of alcohol use.

8) Recurrent alcohol use in situations in which it is physically hazardous.

9) Alcohol use is continued despite knowledge of having a persistent or recurrent physical or psychological problem that is likely to have been caused or exacerbated by alcohol.

10) Tolerance, as defined by either of the following: a) a need for markedly increased amounts of alcohol to achieve intoxication or desired effect; b) a markedly diminished effect with continued use of the same amount of alcohol.

11) withdrawal, as manifested by either of the following:
  a) The characteristic withdrawal syndrome for alcohol:
   i) cessation of (or reduction in) alcohol use that has been heavy and prolonged;
   ii) two (or more) of the following, developing within several hours to a few days after the cessation of (or reduction in) alcohol use: autonomic hyperactivity (e.g. sweating or pulse greater than 100 bpm); increased hand tremor; insomnia; nausea or vomiting; transient visual, tactile, or auditory hallucinations or illusions; psychomotor agitation; anxiety; generalized tonic-clonic seizures.
  b) Alcohol (or a closely related substance, such as benzodiazepine) is taken to relieve or avoid withdrawal symptoms.

"Alcohol use disorder" may be separated into the following three categories: mild (i.e. presence of 2 to 3 symptoms, defined with reference to DSM-5 criteria), moderate (i.e. presence of 4 to 5 symptoms, defined with reference to DSM-5 criteria) and severe (i.e. presence of 6 or more symptoms, defined with reference to DSM-5 criteria). In one embodiment "alcohol use disorder", as used herein, refers to "mild alcohol use disorder", "moderate alcohol use disorder" and "severe alcohol use disorder". In a further embodiment, "alcohol use disorder", as used herein, refers to "mild alcohol use disorder", "moderate alcohol use disorder" or "severe alcohol use disorder".

The term "alcohol use disorder patient" refers to a patient diagnosed with AUD, as defined herein. In one embodiment, the term "alcohol use disorder patient" refers to a patient diagnosed with AUD who is in abstinence from alcohol, for example, for at least 1 day, such as 3 days or more. The term "alcohol use disorder patient in abstinence from alcohol" refers to a patient diagnosed with AUD in abstinence from alcohol for a period, for example, for at least 1 day. The term "binge drinking" refers to an abuser of alcohol (i.e. a heavy drinker). As explained at http://drugabuse.com/library/alcohol-abuse/, abusers of alcohol may not drink on a consistent basis, for example, they may only drink once a week, but, when drinking, they may drink heavily, which will cause problems, such as suffering from alcohol intoxication. For the sake of clarity, herein, an abuser of alcohol is not an alcohol use disorder patient (i.e. does not meet criteria for alcohol use disorder as defined with reference to DSM-5 criteria). The term "heavy drinker" refers to someone with a heavy alcohol use pattern. According to the National Institute on Alcohol Abuse and Alcoholism (NIAAA), the Substance Abuse and Mental Health Services Administration (SAMHSA) defines "heavy alcohol use" as binge drinking on 5 or more days in the past month. NIAAA defines binge drinking as a pattern of drinking that brings blood alcohol concentration (BAC) levels to 0.08 g/dL. This typically occurs after 4 alcoholic drinks for women and 5 alcoholic drinks for men—in about 2 hours. The Substance Abuse and Mental Health Services Administration (SAMHSA), defines "binge drinking" as 5 or more alcoholic drinks for males or 4 or more alcoholic drinks for females on the same occasion (i.e., at the same time or within a couple of hours of each other) on at least 1 day in the past month.

The term "alcohol", as used herein, for example in relation to "drinks", "alcoholic drinks" or "drinking", refers to ethyl alcohol (i.e. ethanol). The term "alcohol craving" as used herein refers to a conscious desire or urge to consume alcohol.

The term "alcohol use", as used herein, refers to alcohol consumption.

The term "reducing alcohol use" or "reduction of alcohol use", as used herein, refers to reducing the amount or frequency of alcohol use, for example as assessed by urinalysis [e.g. by measuring metabolites of alcohol in urine, such as Ethyl Glucuronide (EtG)] or as assessed by using self-reported alcohol use with standardized tools like the Timeline Follow-Back self-report (Sobell L C, Sobell M B, 1996, Timeline FollowBack user's guide: A calendar method for assessing alcohol and drug use. Addiction Research Foundation, Toronto, Ontario, Canada; *J. Anal. Toxicolo.*, 2002, 26: 393-400). In one embodiment, "reducing alcohol use" or "reduction of alcohol use" refers to a reduction in drinks per day, a reduction in drinks per drinking day, or a reduction in the frequency of drinking, such as a reduction in the percentage of drinking days or percentage of heavy drinking days. In another embodiment "reducing alcohol use" or "reduction of alcohol use" refers to an increase in the time to any drinking or time to first heavy drinking day. The term "drinking", "drinks" or "alcoholic drinks", as used herein, is understood in the context of "standard drinks", such as spirits or blends that are intended for human consumption, wherein a "standard drink" equals 12 g ethanol. The term "heavy drinking day", as used herein, refers to a day with a total alcohol consumption ≥60 g of ethanol for men and ≥40 g for women.

The term "alcohol abstinence" or "in abstinence from alcohol", as used herein, refers to not taking alcohol. The term "promoting alcohol abstinence" or "promotion of alcohol abstinence", as used herein, refers to help maintaining abstinence from alcohol use, in particular after at least 1 day of not taking alcohol, for example maintaining abstinence from alcohol use for a period of, for example, at least 1 week, 2 weeks, 3 weeks, 1 month, 3 months, 6 months or more, in particular at least 1 week or more, such as 2 weeks.

The term "relapse into alcohol use" or "relapse into alcohol consumption", as used herein, refers to an alcohol intake (i.e. taking alcohol) following a period of alcohol abstinence, for example following a period of alcohol abstinence of at least 1 day or more, such as 3 days, 1 week, 2 weeks, 3 weeks, 1 month, 3 months, 6 months or more.

The term "preventing relapse into alcohol use" or "preventing relapse into alcohol consumption", as used herein, refers to the prevention of alcohol intake by an AUD patient after the patient has stopped the intake of alcohol, in particular after 1 day or more of not taking alcohol. In some embodiments, the term encompasses the permanent stoppage of alcohol intake. In other embodiments, the term encompasses a delay in the resumption of alcohol intake as compared to the time to resumption by a subject that is not administered a compound of the invention. The delay in resumption can be, e.g., days (e.g., 2, 3, 4, 5, 6, 7 days), weeks (e.g., 1, 2, 3 weeks), months (e.g., 1, 2, 3, 4, 5, 6 months), or longer.

The term "AUD associated with high risk drinking for acute problems", as used herein, refers to alcohol use disorder associated with daily alcohol consumption ≥60 g/day of ethanol for men and ≥40 g/day for women (*International Guide for Monitoring Alcohol Consumption and Related Harm*, WHO/MSD/MSB/00.4; World Health Organization 2000, p. 51: http://www.who.int/iris/handle/10665/66529).

The term "impulsivity", as used herein, refers to a predisposition toward rapid, unplanned reactions to internal or external stimuli with diminished regard to the negative consequences of these reactions to the impulsive individual or others" (Moeller F G at al., *Am J Psychiatry.* 2001; 158: 1783-1793).

The term "psychosocial or behavioral therapy", as used herein, refers to, but not limited to, 12-step facilitation therapy [e.g. NIAAA, Project MATCH Monograph Series. Volume 1, NIH Publication No. 94-3722, (1995) reprinted 1999], cognitive behavioral therapy (e.g. as described in Arch. Gen. Psychiatry 1999; 56:493-502), interpersonal therapy (e.g. as described in *Psychol Addict Behav* 2009; 23(1): 168-174), contingency management based therapy (e.g. as described in *Psychol Addict Behav* 2009; 23(1): 168-174; in *J. Consul. Clin. Psychol.* 2005; 73(2): 354-59; or in *Case Reports in Psychiatry, Vol.* 2012, Article ID 731638), community reinforcement approach based therapy (e.g. as described in *Drug Alcohol Depend* 2004; 74:1-13), motivational interviewing based therapy (e.g. as described in *J. Consul. Clin. Psychol.* 2001; 69(5): 858-62), motivational enhancement based therapy (e.g. as described in *Drug Alcohol Depend* 2007, 91:97-101) or meditation based therapy, such as transcendental meditation based therapy (e.g. as described in Addiction 2004; 99(7):862-874 or *J. Consul. Clin. Psychol.* 2000; 68(3): 515-52); in particular contingency management based therapy.

The term "standardized psychological treatment" or ""standardized psychological support", as used herein, refers to standard counseling sessions, for example once a week, in particular counseling focused on alcohol consumption.

The term "computer-assisted" in the expression "the psychosocial or the behavioral therapy is computer-assisted", as used herein, refers to psychosocial or behavioral therapy comprising the use of electronic tools such as online tools, smartphones, wireless devices or health Apps. In one embodiment, the term "computer-assisted" in the expression "the psychosocial or the behavioral therapy is computer-assisted", as used herein, is to be understood as "computer-implemented" (i.e. the psychosocial or the behavioral therapy is computer-implemented).

The term "administered with food" refers to, for example, any food product, solid or liquid, with caloric content. The dosage of the mavoglurant, or pharmaceutically acceptable salt thereof, may be administered to a subject, for example, between thirty minutes prior to eating food, to, for example, one hour after consumption. In particular, administration of mavoglurant, or pharmaceutically acceptable salt thereof, occurs immediately after consuming food up to about thirty minutes after consumption.

The term "genetic variation" refers to a change in a gene sequence relative to a reference sequence (e.g., a commonly-found and/or wild-type sequence). Genetic variation may be recombination events or mutations such as substitution/deletion/insertion events like point and splice site mutations. In one embodiment, the genetic variation is a genetic variation in mGluR5.

The term "treat" "treating" "treatment" or "therapy", as used herein, means obtaining beneficial or desired results, for example, clinical results. Beneficial or desired results can include, but are not limited to, alleviation of one or more symptoms of alcohol use disorder patients, as defined herein, such as anxiety symptoms or depression symptoms associated with alcohol use disorder, in particular by an alcohol use disorder patient in abstinence from alcohol, as herein defined. One aspect of the treatment is, for example, that said treatment should have a minimal adverse effect on the patient, e.g. the agent used should have a high level of safety, for example without producing the side effects of previously known treatment regimens. The term "alleviation", for example in reference to a symptom of a condition, as used herein, refers to reducing at least one of the frequency and amplitude of a symptom of a condition in a patient.

The term "concomitant", as used herein, for example in relation to "concomitant with methadone or buprenorphine treatment", refers to both simultaneous and sequential administration.

As used herein, the term "subject" refers to a mammalian organism, preferably a human being (male or female).

As used herein, the term "patient" refers to a subject who is diseased and would benefit from the treatment.

As used herein, a subject is "in need of" a treatment if such subject (patient) would benefit biologically, medically or in quality of life from such treatment.

The term "pharmaceutical composition" is defined herein to refer to a mixture or solution containing at least one active ingredient or therapeutic agent to be administered to a subject, in order to treat a particular condition (i.e. disease, disorder or condition or at least one of the clinical symptoms thereof) affecting the subject.

As used herein, the term "pharmaceutically acceptable excipient" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 22$^{nd}$ Ed. Mack Printing Company, 2013, pp. 1049-1070). Except insofar as any conventional carrier is incompatible with the active ingredient, its use in the therapeutic or pharmaceutical compositions is contemplated.

The terms "drug", "active substance", "active ingredient", "pharmaceutically active ingredient", "active agent" or "therapeutic agent" are to be understood as meaning a compound in free form or in the form of a pharmaceutically acceptable salt, in particular compounds of the type specified herein. In particular, reference to mavoglurant, or a pharmaceutically acceptable salt thereof, in combination with a further active agent, as used herein (e.g. in any of embodiments (a) to (j), herein above, or in any of the claims, herein below), refers to mavoglurant in combination with at least one further active agent selected from the group consisting of an opioid antagonist (e.g. nalmefene, naltrexone), a CB-1 antagonist (e.g. rimonabant), a CRH1 receptor antagonist (e.g. verucerfont, pexacerfont), a NK1R antagonist (e.g. tradipitant), an OTR agonist (e.g. oxytocin), a GABA agent (e.g. topiramate, baclofen, a benzodiazepine, such as alprazolam, diazepam or lorazepam), a voltage-gated sodium channel inhibitor (e.g. oxacarbazepine, valproic acid, zonisamide), a voltage-dependent calcium channel agonist (e.g. gabapentin, pregabalin), a α7 nicotinic acetylcholine receptor agonist (e.g. varenicline), a 5-HT$_3$ antagonist (e.g. ondansetron), a 5-HT$_{1A}$ receptor partial agonist (e.g. aripiprazole), a 5-HT$_{2A}$ receptor antagonist (e.g. quetiapine, olanzapine, mirtazapine), a 5-HT reuptake inhibitor (e.g. trazodone), a SERT inhibitor (e.g. duloxetine), a α1 adrenoreceptor antagonist (e.g. doxazosin, prazosin), a glucocorticoid receptor antagonist (e.g. mifepristone), a α1 adrenoreceptor agonist (e.g. guanfacine), an AChE inhibitor (e.g. citicoline), a dopamine D2 receptor antagonist (e.g. tiapride), a α2 adrenoreceptor agonist (e.g. clonidine), an NMDA receptor antagonist (e.g. acamprosate) and an aldehyde dehydrogenase inhibitor (e.g. disulfiram); or pharmaceutically acceptable salts thereof.

The term "immediate release form" refers to a pharmaceutical composition designed to release the active substance immediately upon in vivo administration.

The term "modified release form" refers to a pharmaceutical composition which releases the active substance not immediately, but offers a sustained, retard, continuous, gradual, prolonged or pulsatile release and therefore alters drug plasma levels distinctively versus an immediate release form. The term "modified release form" encompasses forms that are described as controlled-release form, sustained-release form, extended-release form, and long-acting form; in particular a sustained-release form.

The term "combination" or "pharmaceutical combination" refers to either a fixed combination in one unit dosage form (e.g., capsule, tablet, caplets or particulates), non-fixed combination, or a kit of parts for the combined administration where a compound of the present invention and one or more combination partner (e.g. another drug as specified herein, also referred to as further "pharmaceutical active ingredient", "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "fixed combination" means that the active ingredients, e.g. the compound of the present invention and one or more combination partners, are both administered to a patient simultaneously in the form of a single entity or dosage. The term "non-fixed combination" means that the active ingredients, e.g. a compound of the present invention and one or more combination partners, are both administered to a patient as separate entities either simultaneously or sequentially with no specific time limits, wherein such administration provides therapeutically effective levels of the two compounds in the body of the patient.

The compound of the present invention may be administered separately, by the same or different route of administration, or together in the same pharmaceutical composition as the other agents. In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

As used herein, the term "a," "an," "the" and similar terms used in the context of the present invention (especially in the context of the claims) are to be construed to cover both the singular and plural unless otherwise indicated herein or clearly contradicted by the context.

The use of any and all examples, or exemplary language (e.g. "such as") provided herein is intended merely to better illuminate the invention and does not pose a limitation on the scope of the invention otherwise claimed.

As used herein, the compound of the invention, alternatively named Compound (I), as used herein above and below, is the mGluR5 antagonist (−)-(3aR,4S,7aR)-4-Hydroxy-4-m-tolylethynyl-octahydro-indole-1-carboxylic acid methyl ester, also named (−)-(3aR,4S,7aR)-4-Hydroxy-4-[2-(3-methylphenyl)ethynyl]perhydroindole-1-carboxylic acid methyl ester, also known as mavoglurant, of formula:

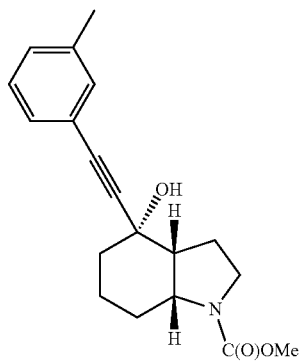

which can be e.g. prepared as described in WO2003/047581, e.g., in Example 1, or as described in WO2010/018154. WO2003/047581, which is incorporated herein by reference, also describes its in-vitro biological data, as per page 7. As used herein, mavoglurant refers to the free form, and any reference to a pharmaceutically acceptable salt thereof refers to a pharmaceutically acceptable acid addition salt thereof. As used herein, the term mavoglurant, or a salt thereof, such as a pharmaceutically acceptable salt thereof, as used in the context of the present invention (especially in the context of the any of the embodiments, above or below, and the claims) is thus to be construed to cover both the free form and a pharmaceutically acceptable salt thereof, unless otherwise indicated herein.

In one embodiment, Compound (I) is also intended to represent isotopically labeled forms. Isotopically labeled compounds have structures depicted by the formula above except that one or more atoms are replaced by an atom having a selected atomic mass or mass number. Isotopes that can be incorporated into the compound of the invention include, for example, isotopes of hydrogen, namely the compound of formula:

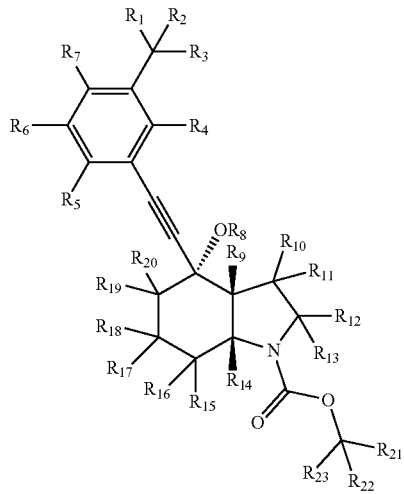

wherein each $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{23}$ is independently selected from H or deuterium; provided that there is at least one deuterium present in the compound. In other embodiments there are multiple deuterium atoms present in the compound.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of the compound of the invention. The concentration of deuterium, may be defined by the isotopic enrichment factor. The term "isotopic enrichment factor" as used herein means the ratio between the isotopic abundance and the natural abundance of a specified isotope. If a substituent in the compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into the compound of the invention include isotopes of hydrogen, other than deuterium, carbon, nitrogen, oxygen, and fluorine such as $^3H$, $^{11}C$, $^{13}C$, $^{14}C$, $^{15}N$, $^{18}F$ respectively. Accordingly it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. The isotopically-labeled compounds can generally be prepared by conventional techniques known to those skilled in the art or by processes analogous to those described preparation of the compound of the invention by using an appropriate isotopically-labeled reagents in place of the non-labeled reagent previously employed.

As used herein, the terms "free form" or "free forms" refers to the compound in non-salt form, such as the base free form or the acid free form of a respective compound, e.g. the compounds specified herein (e.g. mavoglurant or further pharmaceutical active ingredient, for example, as defined herein).

As used herein, the terms "salt", "salts" or "salt form" refers to an acid addition or base addition salt of a respective compound, e.g. the compounds specified herein (e.g. mavoglurant or further pharmaceutical active ingredient, for example, as defined herein). "Salts" include in particular "pharmaceutically acceptable salts". The term "pharmaceutically acceptable salts" refers to salts that retain the biological effectiveness and properties of the compounds and, which typically are not biologically or otherwise undesirable. The compounds, as specified herein (e.g. mavoglurant or further pharmaceutical active ingredient, for example, as defined herein), may be capable of forming acid and/or base salts by virtue of the presence of amino and/or carboxyl groups or groups similar thereto. The compound of the invention is capable of forming acid addition salts, thus, as used herein, the term pharmaceutically acceptable salt of mavoglurant means a pharmaceutically acceptable acid addition salt of mavoglurant.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Pharmaceutically acceptable salts can be synthesized from a basic or acidic moiety, by conventional chemical methods. Generally, such salts can be prepared by reacting the free acid forms of the compound with a stoichiometric amount of the appropriate base (such as Na, Ca, Mg, or K hydroxide, carbonate, bicarbonate or the like), or by reacting the free base form of the compound with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", $22^{nd}$ edition, Mack Publishing Company (2013); and in "Handbook of Pharmaceutical Salts: Properties, Selection, and Use" by Stahl and Wermuth (Wiley-VCH, Weinheim, 2011, $2^{nd}$ edition).

The compounds specified herein (e.g. mavoglurant or the further pharmaceutical active ingredient, for example, as defined herein) can be administered by conventional route, in particular orally, such as in the form of tablets, capsules, caplets or particulates, which can be manufactured according to pharmaceutical techniques as known in the art (for example in "Remington Essentials of Pharmaceutics, 2013, $1^{st}$ Edition, edited by Linda Felton, published by Pharmaceutical Press 2012, ISBN 978 0 85711 105 0; in particular Chapter 30), wherein pharmaceutical excipients are, for example, as described in "Handbook of Pharmaceutical Excipients, 2012, $7^{th}$ Edition, edited by Raymond C. Rowe, Paul J. Sheskey, Walter G. Cook and Marian E. Fenton, ISBN 978 0 85711 027 5". In particular, WO2014/199316 describes formulations comprising mavoglurant, in particular modified release formulations thereof, and is incorporated herein by reference, more particularly the Examples, the preferred embodiments and claims therein.

The pharmaceutical composition or combination of the present invention can be in a unit dosage form (e.g. tablet, capsule, caplet or particulate) comprising an amount ranging of from 1 mg to 300 mg, in particular of from 50 mg to 200 mg, such as 50 mg to 100 mg, more particularly 200 mg, of mavoglurant (referring to an amount of the free form of mavoglurant, and if a salt thereof is used the amount will be adapted accordingly; in particular mavoglurant is in the free form). For the above-mentioned uses/treatment methods the appropriate dosage may vary depending upon a variety of factors, such as, for example, the age, weight, sex, the route of administration or salt employed. In patients with, for example, of from 50-70 kg body weight, an indicated daily dosage is, for example, 200 mg/b.i.d (referring to an amount of the free form of mavoglurant, and if a salt thereof is used the amount will be adapted accordingly).

Abbreviations

BE=Benzoylecgonine
EtG=Ethyl Glucuronide
CM=Contingency Management
DSM 5=Diagnostic and Statistical Manual of Mental Disorders, 5th Ed.
AUD=Alcohol Use Disorder
CUD=Cocaine Use Disorder
PK=Pharmacokinetic
TLFB=Timeline Follow-Back
mg=milligram
bid=b.i.d=twice (two times) a day
mmHg=millimiter of mercury
msec=millisecond
HIV=human immunodeficiency virus
ELISA=enzyme-linked immunosorbent assay
ECG=electrocardiogram
QT=time between the start of the Q wave and the end of the T wave
T wave=positive deflection after each QRS complex
ST wave=time between the start of the S wave and the end of the T wave
QRS=time between the start of the Q wave and the end of the T wave
QTcF=Fridericia QT correction formula
SoA=standard of care
SSRI=Selective serotonin reuptake inhibitors
C-SSRS=Columbia Suicide Severity Rating Scale
hCG=human chorionic gonadotropin
AST=aspartate aminotransferase
ALT=alanine aminotransferase
ULN=upper limit of normal
GGT=gamma-glutamyl transpeptidase
AV block=Atrioventricular block
UDS=urinary drug screening
MDMA=3,4-methylenedioxy-methamphetamine
MDEA=3,4-methylenedioxy-N-ethylamphetamine
MDA=3,4-methylenedioxy-amphetamine

EXAMPLES

The following Examples serve to illustrate the invention without limiting the scope thereof. The term "mavoglurant", as used in the context of these examples, refers to the free form.

Example 1

Evaluation of the Effects of Mavoglurant on Cocaine Dependence and Cocaine Reinstatement Using the Intravenous Self-Administration Model in Sprague-Dawley Rats Animals Adult male Sprague-Dawley rats (300-325 g at arrival) from Harlan Laboratory (Indiana, USA) were used. Upon arrival, the rats were assigned a unique identification numbers (tail marks). Animals were single housed in suspended polycarbonate rat cages with filter tops, and were acclimated for up to 7 days. All rats were examined, handled, and weighed prior to initiation of the study to assure adequate health and suitability. During the course of the study, 12 h/12 h light/dark cycles were maintained. The room temperature was 21-23° C. with a relative humidity maintained at 30-70%. Water was provided ad libitum for the duration of the study.

Test Compounds

Cocaine Hydrochloride (Sigma-Aldrich, USA) (1.05 mg/ml which is equivalent to 0.3 mg/kg/infusion under 350 g body weight and 0.1 ml/infusion rate) was dissolved in saline (0.9% NaCl). The formulation was a clear solution.

Mavoglurant (free form) was formulated in 0.5% methylcellulose (MC) at 1, 3 and 10 mg/kg and administered orally at a dose volume of 1 ml/kg 60 minutes prior to test.

Apparatus

Intravenous drug self-administration took place in sound attenuated operant chambers equipped with an exhaust fan (Med Associates, VT). Each chamber contained two levers situated on one wall of the chamber. Only one of the two levers was active (located on the left side). Pressing the active lever caused delivery of reinforcer (food or cocaine). The other lever was "inactive", i.e. pressing it did not deliver any reinforcement. A stimulus light was located above each lever, but only the one above the active lever was on during the timeout period (defined below). A house light (providing illumination) was located at the top of opposite wall. For food training (see details below), a pellet receptacle was situated between the two levers for delivery of food pellets (Bio-Serv's Dustless Precision Pellets #F0165, 45 mg). An infusion pump mounted above each chamber delivered drug solution via Tygon tubing connected to a single channel fluid swivel, which was mounted on a balance arm above the operant chamber. The output of the liquid swivel was attached to the externalized terminus of the intravenous catheter.

Methods

Phase I: Acute Effects of Mavoglurant on Cocaine Self-Administration in Rats

Food Training and Surgery

Prior to intravenous catheterization surgery, rats were trained to press the active lever to obtain food. Food training started after the rats were food-restricted and reached approximately 85% of the free-feeding body weight. After acquiring the lever-press response to obtain food, rats were implanted with a jugular vein catheter (Access Technologies, USA). Catheters were flushed daily with a 0.2 ml Heparin-Enrofloxacin solution to avoid clogging and to ensure smooth drug infusion. The flushing liquid was made in 50 ml volume unit which contained 1500U Heparin and 320 mg Enrofloxacin (Baytril®). The solution was stored in sterilized vials in 4° C. refrigerator. The rats were on free feeding two days prior to surgery and throughout recovery.

During the study, Methohexital sodium (Brevital®, Henry Schein Animal Health, USA) was used to confirm proper infusion via the implanted catheter. Brevital is a short-acting barbiturate that, when infused through the catheter, produces overt signs of sedation within seconds. The Brevital test (0.2 ml of 1% solution) was performed after acquisition sessions of both Phases and after compound test session of Phase I. Animals that showed no immediate signs of sedation were removed from the experiment.

Acquisition of the Cocaine Self-Administration Response

One week after the surgery, single housed rats were food restricted and maintained at ~85% of their free-feeding age-matched control body weight throughout the study. Rats were then allowed to self-administer cocaine by pressing the active lever on a fixed-ratio (FR) schedule of reinforcement. In this study a FR5 schedule was used, i.e. five lever presses for one cocaine delivery. The dose of cocaine was 0.3 mg/kg/infusion, which equals to 0.105 mg per rat (350 g) in each infusion (0.1 ml solution). Each cocaine infusion lasted 1.0 sec. Delivery of cocaine was followed by a 20 second timeout period, during which no drug was delivered even if the active lever was pressed. During timeout, the stimulus light above the active lever was on. After 15 days of training, all rats demonstrated a high and stable number of lever presses for cocaine. Each training or testing session lasted 1 hour.

Pharmacological Treatment with Mavoglurant

Pharmacological studies were initiated after a stable cocaine self-administration baseline was established (less than 20% variation in daily amount of drug infusions over 3 consecutive days; a minimum of 6 drug infusions per session). Pharmacological studies were conducted twice a week (usually on Wednesday and Friday), and baseline cocaine training were maintained on other days.

N=12
Vehicle
Mavoglurant 1 mg/kg
Mavoglurant 3 mg/kg
Mavoglurant 10 mg/kg

Phase II: Effects of Mavoglurant on Cue-Induced Reinstatement of the Self-Administration Response Food Training and Surgery The methods for food training, catheter surgery, flushing and infusion confirmation were the same as those in Phase I.

Acquisition

Cocaine self-administration training in this stage was conducted in a separate cohort of rats (N=32). The methods of training were the same as those in Phase I, but the cues (light flash plus tone) appeared concurrently during cocaine infusion, and the cue light stayed on during the 20 second timeout period. As in Phase I, rats underwent 15 days of acquisition training.

Extinction and Cue-Induced Reinstatement

After a stable rate of cocaine self-administration was achieved, the rats underwent a 9-day extinction procedure, which was similar to acquisition training except that pressing the active lever led to saline infusion instead of cocaine. During extinction sessions no cues were presented after an active lever-press. Rats were all reached the criterion for extinction (number of infusions ≤5, i.e. number of active lever responses <30 in the 1-hour session) in day 9 (last day) of extinction training.

During the reinstatement session, which occurred one day after the last extinction session, rats were presented the cues (flash+tone) at the beginning of the session and their lever-press responses recorded. There was no cocaine infusion during this reinstatement session, subject only received saline on a FR5 schedule. An independent groups design was used for this study, i.e. ~half of rats (N=15 after infusion confirmation) were administered with an optimal dose of Mavoglurant and ~half (N=14 after infusion confirmation) with vehicle before the reinstatement session. Based on the results of Phase I, the optimal dose of Mavoglurant used in Phase II was 10 mg/kg.

Results

Phase I: Acute Effects of Mavoglurant on Cocaine Self-Administration

Acquisition of Cocaine Dependence

The acquisition of the cocaine self-administration response in Phase I is illustrated in FIG. 1. Twelve rats per group were included in this study after confirmation of proper infusion with Brevital. Cocaine self-administration increased steadily during the first week of training and stabilized during the second week of training. Learning was confirmed by a two-way ANOVA (Training day effect: F[14,330]=6.199; P<0.001). There was also a significant group x day interaction (F[1,330]=4.850, P<0.05), however post hoc comparisons did not indicate any significant differences between groups on each training day, thus confirming comparable self-administration performance between groups (sub-cohorts).

Acute Effects Mavoglurant on Cocaine Self-Administration

For sub-cohort I-b, a one-way ANOVA with repeated measures confirmed a significant effect of mavoglurant [Treatment effect: F(3,33)=6.358; P<0.01]. Post hoc comparisons further confirmed that mavoglurant tended to reduce responding on the active lever at 3 mg/kg (p<0.10) and significantly reduced responding at 10 mg/kg (p<0.001).

Figure 3:
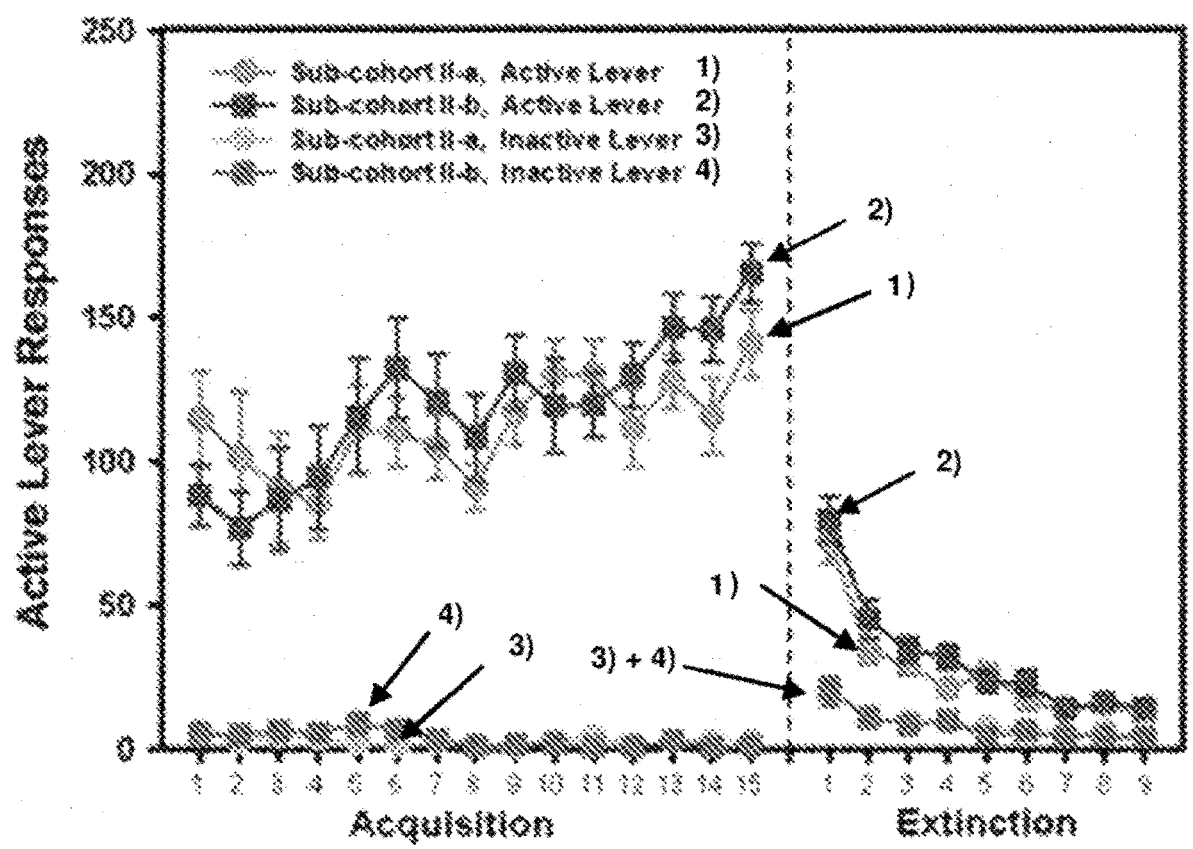
FIG. 3: Acquisition and extinction of the cocaine self-administration response in two sub-cohorts of rats (Phase II). Data represent the means+SEM. N=14-15 per group.

Phase II: Effects of Mavoglurant on Cue-Induced Reinstatement of Self-Administration Acquisition and Extinction of Cocaine Dependence Acquisition of the cocaine self-administration response is illustrated in FIG. 3. The two groups (sub-cohorts) included 14 and 15 rats after confirmation of proper infusion with Brevital. Like in Phase I, cocaine self-administration increased steadily during the first week of training and stabilized during the second week of training. A two-way ANOVA confirmed a significant effect of training day (F[14,405]=3.463; P<0.001) and no differences between sub-cohorts (F[1,405]=1.538, n.s., indicating comparable learning performance between groups.

During the extinction phase there was a progressive and significant reduction of responses on the active lever, which was confirmed by a two-way ANOVA (Day effect: F[8,243]=41.635; P<0.001). There was also a significant main effects of sub-cohorts (F[1,243]=5.306, P<0.05), however post hoc comparisons indicated comparable performance between groups during each extinction session. All rats reached the criteria for extinction by 9 days of training.

Cue-Induced Reinstatement of the Self-Administration Response

The effects of vehicle and mavoglurant (10 mg/kg, PO, 1 hour prior to test) on cue-induced reinstatement of the self-administration response are illustrated in FIG. 4. Two-way ANOVAs confirmed a significant effect of session (extinction vs. reinstatement, F[1,54]=12,690; P<0.001), a significant treatment effect (vehicle vs. mavoglurant, F[1,54]=8.194; P<0.01) and a significant treatment x session interaction (F[1,54]=12,805; P<0.001). Post hoc analyses indicated that the session effect was solely attributed by vehicle treatment, i.e. while cue induced a significant reinstatement of active lever-pressing (P<0.001), cue-induced reinstatement was suppressed in mavoglurant-treated rats.

CONCLUSIONS

The present study investigated the efficacy of mavoglurant in a rat model of cocaine self-administration and a model of relapse for cocaine intake (i.e. cue-induced reinstatement). mavoglurant (10 mg/kg, PO, 1 hour prior to test) significantly reduced cocaine self-administration in rats.

Moreover, after extinction of the self-administration response, mavoglurant (10 mg/kg, PO, 1 hour prior to test) completely prevented cue-induced reinstatement of the self-administration response.

In conclusion, the present study indicated that mavoglurant is efficacious in a rat model of cocaine self-administration, as well as in a model of relapse. Based on these results and the known role of mGluR5 receptors in substance use disorders (e.g. in *Glutamate-based therapies for psychiatric disorders*, Springer 2000, ISBN 978-3-0346-0240-2, p. 133-147: Metabotropic glutamate receptors as targets for the treatment of drug and alcohol dependence), it is expected that the mGluR5 antagonist mavoglurant will be efficacious in a model of alcohol self-administration and a model of relapse for alcohol. Similarly, preclinical models have shown that other mGluR5 antagonists, such as MPEP [i.e. 2-methyl-6-(2-phenylethynyl)pyridine], which decreased cocaine self-administration in mice (e.g. in Chiamulera, C. et al., *Nat. Neurosci.* 2001, 4, 873-874), decreased cocaine self-administration in rats (e.g. in Kenny, P. J. et al., *Behav. Pharmacol.* 14, S55) and also decreased ethanol self-administration in mice (e.g. in Sharko, A. C. et al., *Soc. Neurosci. Abstr.* 783.781, 2002) or such as MTEP [i.e. 3-[2-(2-methylthiazol-4-yl)ethynyl]pyridine], which decreased ethanol consumption in mice (e.g. in Olive, M. F., et al, *Mol. Pharmacol.,* 2005, 67:349-3550) and decreased cocaine self-administration in rats (Martin-Fardon R., et al., *J. Pharmacol Exp Ther* 2009, 329(3): 1084).

2. Clinical Testing

Clinical testing of mavoglurant may be conducted, for example, according to standard clinical practice (e.g. placebo control study in patients with alcohol use disorder, such as those in clinicaltrials.gov; in opentrials.net), for example, by dosing 200 mg b.i.d/modified release formulation (free form).

The invention claimed is:

1. A method for reduction of alcohol use by an alcohol use disorder patient, in need thereof, comprising administering to said alcohol use disorder patient 200 mg/b.i.d. of mavoglurant, or a pharmaceutically acceptable salt thereof.

2. A method according to claim 1, wherein alcohol use disorder is associated with high risk drinking for acute problems.

3. A method according to claim 1, wherein alcohol use disorder is comorbid with a psychiatric disorder.

4. A method according to claim 1, wherein administration of mavoglurant, or a pharmaceutically acceptable salt thereof is combined with standardized psychological treatment.

5. A method according to claim 1, wherein administration of mavoglurant, or a pharmaceutically acceptable salt thereof is combined with psychosocial or behavioral therapy or combination thereof.

6. A method according to claim 5, wherein the psychosocial or the behavioral therapy is computer-assisted.

7. A method according to claim 1, wherein administration of mavoglurant, or a pharmaceutically acceptable salt thereof, is concomitant with methadone or buprenorphine treatment.

8. A method according to claim 1, wherein mavoglurant, or a pharmaceutically acceptable salt thereof, is administered in combination with a further active agent.

9. A method according to claim 1, wherein the patient has a genetic variation associated with a substance use disorder.

10. A method according to claim 1, wherein mavoglurant, or a pharmaceutically acceptable salt thereof, is administered in an immediate-release form or a modified release form.

11. A method according to claim 1, wherein alcohol use disorder is associated with daily alcohol consumption 60 g/day of ethanol for men and 40 g/day for women.

12. A method according to claim 3, wherein the psychiatric disorder is chosen from antisocial personality disorder, borderline personality disorder, depression, anxiety, schizophrenia, attention deficit hyperactivity disorder, bipolar disorder, obsessive compulsive disorder, and binge eating disorder.

13. A method according to claim 9, wherein the patient has a genetic variation associated with alcohol use disorder.

* * * * *